(12) United States Patent
Norrie et al.

(10) Patent No.: US 7,708,732 B2
(45) Date of Patent: May 4, 2010

(54) METHODS OF ADMINISTERING THERAPEUTIC INJECTIONS

(75) Inventors: Jayme Norrie, Draper, UT (US); Hans Himbert, Bromma (SE); Maria Benktzon, Bromma (SE); Ulrika Vejbrink, Bromma (SE)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 938 days.

(21) Appl. No.: 10/966,364

(22) Filed: Oct. 15, 2004

(65) Prior Publication Data

US 2005/0165381 A1 Jul. 28, 2005

Related U.S. Application Data

(60) Provisional application No. 60/511,956, filed on Oct. 16, 2003.

(51) Int. Cl.
*A61M 31/00* (2006.01)
*A61M 5/315* (2006.01)

(52) U.S. Cl. .................. 604/506; 604/223; 604/228

(58) Field of Classification Search .............. 604/506, 604/187, 198, 208–211, 218, 220, 221, 223, 604/224, 227, 228
See application file for complete search history.

(56) References Cited

U.S. PATENT DOCUMENTS

| 201,443 | A | * | 3/1878 | Parker | 604/209 |
|---|---|---|---|---|---|
| 2,754,818 | A | * | 7/1956 | Scherer | 604/68 |
| 4,194,505 | A | * | 3/1980 | Schmitz | 604/138 |
| 4,444,560 | A | * | 4/1984 | Jacklich | 604/224 |
| 4,457,712 | A | * | 7/1984 | Dragan | 433/90 |
| 4,710,178 | A | * | 12/1987 | Henri et al. | 604/209 |
| 4,970,824 | A | * | 11/1990 | Visser | 47/86 |
| 5,195,663 | A | * | 3/1993 | Martin et al. | 222/327 |
| 5,433,352 | A | * | 7/1995 | Ronvig | 222/391 |
| 5,505,704 | A | * | 4/1996 | Pawelka et al. | 604/191 |
| 5,584,815 | A | * | 12/1996 | Pawelka et al. | 604/191 |
| 6,077,247 | A | * | 6/2000 | Marshall et al. | 604/156 |
| 6,273,861 | B1 | * | 8/2001 | Bates et al. | 600/567 |
| 6,454,746 | B1 | * | 9/2002 | Bydlon et al. | 604/227 |
| 6,599,272 | B1 | * | 7/2003 | Hjertman et al. | 604/209 |
| 7,011,234 | B2 | * | 3/2006 | Stradella | 222/129 |
| 2005/0085776 | A1 | * | 4/2005 | Hommann et al. | 604/207 |

* cited by examiner

*Primary Examiner*—Kevin C Sirmons
*Assistant Examiner*—Andrew M Gilbert
(74) *Attorney, Agent, or Firm*—Stoel Rives LLP

(57) ABSTRACT

Methods of administering an injection are provided including methods of administering injections by individuals exhibiting deteriorated motor skills or impaired hand function. The method includes establishing a hand position about an injection device, including placing at least a one digit of a user' hand about the injection device and placing at least one other digit of a user's hand upon an actuator of the injection device. The hand position is substantially maintained while the injection device is manipulated and positioned to insert a needle at one end thereof into a portion of the user's skin. The hand position is substantially maintained while the user displaces the actuator of the injection device with the at least one other digit in a direction which is substantially transverse to an axis defined between a first end of the injection device and a second end of the device, the needle being located at the second end of the device.

27 Claims, 17 Drawing Sheets

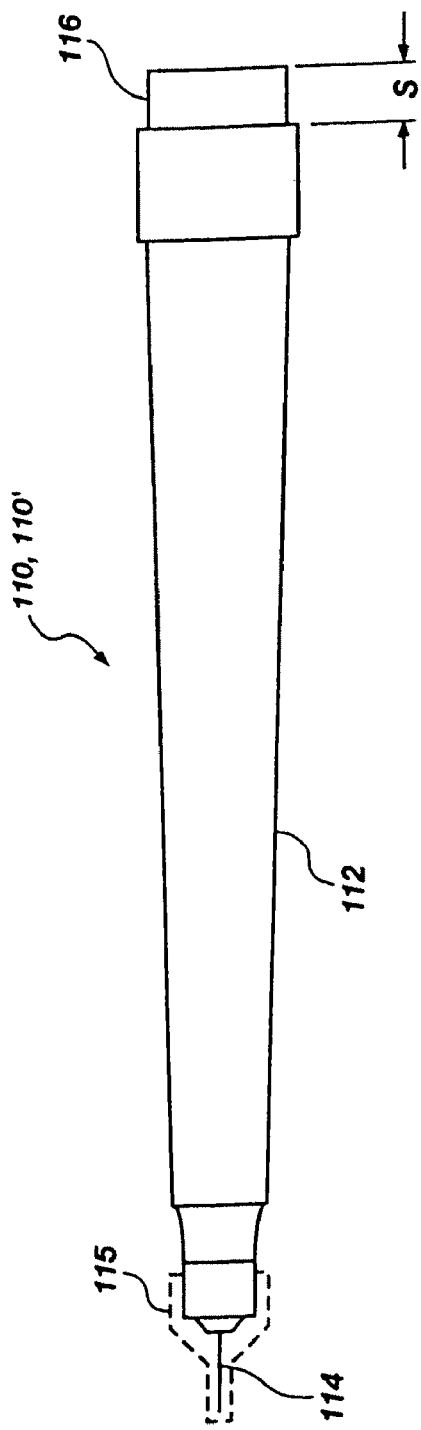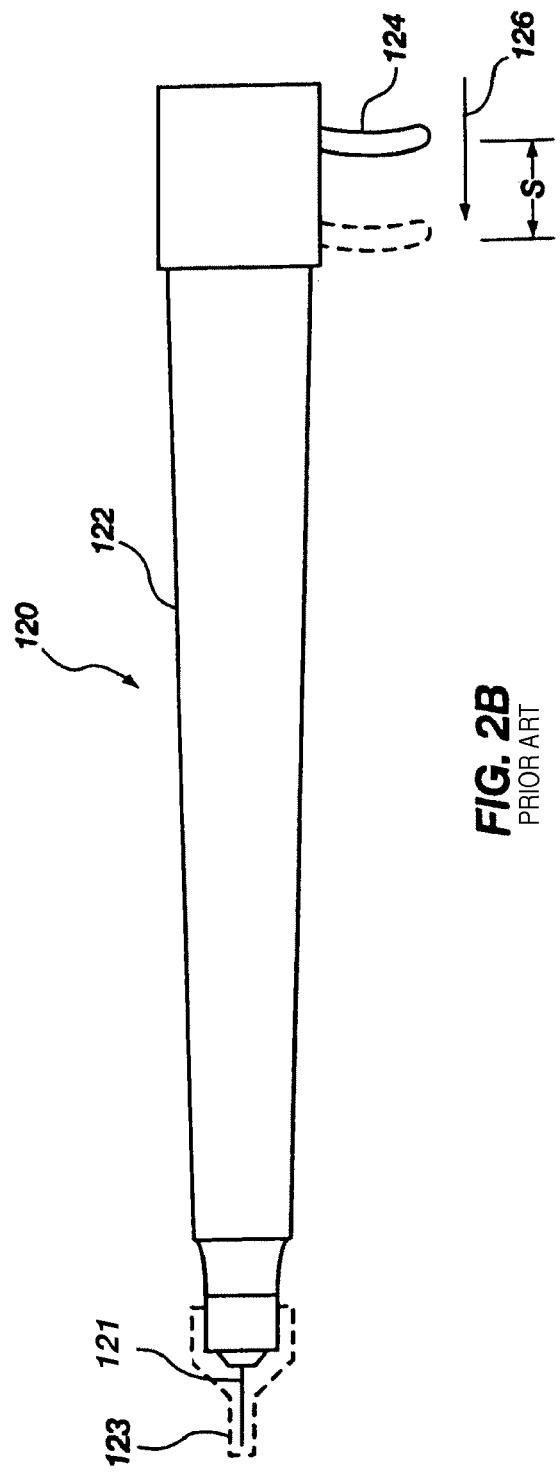
FIG. 2A PRIOR ART
FIG. 2B PRIOR ART

METHODS OF ADMINISTERING THERAPEUTIC INJECTIONS

CROSS-REFERENCE TO RELATED APPLICATION

This application claims the benefit of U.S. Provisional Patent Application Ser. No. 60/511,956, filed Oct. 16, 2003 for METHODS OF ADMINISTERING THERAPEUTIC INJECTIONS, the disclosure of which is incorporated by reference in its entirety.

FIELD OF THE INVENTION

The present invention relates to methods for administering an injection of a fluid product and related injection devices. More particularly, the present invention relates to methods of administering therapeutic injections such as, for example, by individuals with impaired and function, and to injection devices utilized for administering such injections.

BACKGROUND OF THE INVENTION

Numerous injection devices are available for the administration of various medical, pharmaceutical and cosmetic fluid products, including, for example, administration of insulin, and growth hormones. Such injection devices include so-called injection pens (or pen injectors) which are generally shaped and configured like a large pen and are conventionally utilized for self-administered injections. Injection pens may comprise a casing or housing in which is disposed the fluid to be administered. Such fluid is often contained in a second housing, such as a carpoule (also referred to as an ampoule), which may be removable and replaceable with respect to the injector housing. An injection needle or cannula may be placed in communication with the fluid product and configured to deliver the fluid product therethrough upon actuation of the injection device. The injection device may additionally include various mechanisms disposed within the injector housing which enable the administration of the fluid product through the needle in accordance with one or more specified requirements.

For example, a known mechanism for dispensing the fluid product from the container includes a manually deployed actuator that causes displacement of the fluid product from its associated container through the associated needle. Additionally, many injection devices include a mechanism for user adjustment of the dosage or volume of material which is to be delivered through the needle upon deployment of the dispensing actuator. In other injection devices, the dosage may be pre-set or predetermined such that a consistent volume of fluid product is dispensed each time the dispensing actuator is deployed or triggered. A mechanism may be configured to indicate, for example, a selected dosage, a cumulative total of fluid product which has been dispensed from a given container, or a residual amount of the product still remaining in the container. A conventional injection device which includes some of the above listed features is disclosed in U.S. Pat. No. 5,279,586 to Balkwill.

Many conventional injection devices, including those disclosed by the Balkwill patent, have manual actuating mechanisms that require displacement thereof in a direction that is collinear with a longitudinal axis of the injection device's housing. In other words, the actuator is often disposed at an end of the injection device opposite the needle or cannula and must be displaced in a direction towards the needle or cannula in order to effect dispensing of a fluid product. Thus, in operation, such conventional devices are often grasped in the palm of a user's hand with the user's fingers wrapping therearound to form a fist. The user may then position the injection device so as to insert the needle into the user's skin in anticipation of delivering the fluid product. The actuator of the device is then displaced by application of force thereto by a user's thumb. Alternatively, a user may grasp such an injection device between his or her thumb and at least one finger, such as their middle finger, and then displace the actuator with his or her forefinger. In either case, the displacement of the actuator at the end of the injection device can be awkward and difficult for many individuals.

For example, elderly individuals or individuals with impaired hand function may lack the dexterity, motor skills, strength, or a combination thereof, to actuate the injection device while maintaining a firm grasp. Thus, individuals with arthritis or some other ailment affecting the use of their hands may have considerable difficulty in administering therapeutic injections. Ultimately, the difficulty in administering such injections may result in noncompliance by a user with regard to the regular administration of injections in accordance with a prescribed treatment.

Another injection device which employs a different actuation mechanism configuration is disclosed in U.S. Pat. No. 5,584,815 to Pawelka et al. The Pawelka patent generally discloses an injection device having a wing member extendable from one side, wherein pivotal displacement of the wing actuates a dispensing mechanism for delivery of a fluid product through its associated needle and also resets a dosage indicator to an initial zero position. Thus, in operation, a user clasps the circumference of the injection apparatus and pushes the wing into the interior of the apparatus, such that it is angularly displaced about a pivot or fulcrum point.

However, the device disclosed in the Pawelka patent may be prone to an inadvertent discharge or dispensing of fluid during the act of inserting the needle into a user's skin. For example, since the fulcrum of wing actuator is designed such that a user's hand will be positioned between the fulcrum of the wing and the needle during operation, a user may inadvertently displace the wing while grasping the injection device and applying a force in the direction of the needle, as is required to insert the needle into the user's skin. Thus, the user of the device may not receive the proper amount of fluid during the injection, as some fluid become lost during the inadvertent displacement of the wing. While it is recognized that a user may position their hand at a different location during insertion of the needle and then reposition their hand after such insertion, such a process may be laborious and difficult for those with poor motor skills or those that exhibit impaired hand function.

In view of the shortcomings in the art, it would be advantageous to provide a method and device which enables individuals with poor motor skills or with impaired hand function to consistently administer injections in a safe, simple, and accurate manner. It would further be desirable to provide such a method and device which minimize the number of actions required by the user and simplifies the injection process.

BRIEF SUMMARY OF THE INVENTION

In accordance with one aspect of the present invention, a method of administering an injection is provided. The method includes providing an injection device that has a housing defined, at least in part, by a first end and a second end. The injection device further includes a needle disposed proximate the second end, and an actuator disposed between the first and second end. The injection device is grasped by a user and a hand position is established. Establishing the hand position includes placing a thumb at or adjacent the first end of the injection device (opposite the second end) and placing at least one finger on the actuator. The needle of the injection device is inserted into a portion of skin by applying a force to the injection device at least through the thumb. The hand position is substantially maintained while inserting the needle into the user's skin and while displacing the actuator with the at least one finger. The actuator is displaced with the at least one finger in a direction substantially transverse to an axis, defined between the first end and the second end, to effect delivery of a fluid product through the needle.

In accordance with another aspect of the invention, another method of administering an injection is provided. The method includes providing an injection device that has a housing defined, at least in part, by a first end and a second end. The injection device further includes a needle disposed proximate the second end and an actuator disposed between the first end and the second end. The injection device is grasped by a user and a hand position is established. Establishing the hand position includes placing at least one digit around a portion of the housing at a location between the first end and second end and placing at least one other digit on the actuator. The needle is inserted into a portion of skin by applying a force to the injection device in the direction of the needle with at least one digit. The hand position is substantially maintained while inserting the needle into the user's skin and while displacing the actuator with at least one other digit. The actuator is displaced by at least one other digit in a direction substantially transverse to an axis defined between the first end and the second end to effect delivery of a fluid product through the needle.

In accordance with a further aspect of the invention, yet another method of administering an injection is provided. The method includes providing an injection device having a housing defined, at least in part, by a first end and a second end. The injection device further includes a needle disposed proximate the second end and an actuator disposed between the first end and the second end. The injection device is grasped and a hand position is established. Establishing the hand position includes placing at least one digit around a portion of the housing at a location between the first end and the second end, and placing at least one other digit on the actuator. The needle is inserted into a portion of skin by applying a force to the injection device in the direction of the needle through at least one digit. The actuator is displaced by the at least one other digit in a direction substantially transverse to an axis defined between the first end and the second end to effect delivery of a fluid product through the needle. Displacement of the actuator includes rotating the actuator about a pivot that is located between the second end of the injection device and the at least one other digit.

BRIEF DESCRIPTION OF THE SEVERAL VIEWS OF THE DRAWINGS

The foregoing and other advantages of the invention will become apparent upon reading the following detailed description and upon reference to the drawings in which:

FIGS. 2A-2D show various exemplary injection devices utilized in conjunction with various studies of injection administration conducted with patients exhibiting different levels of motor skills and hand function;

DETAILED DESCRIPTION OF THE INVENTION

The present invention is directed to methods of administering injections and related devices for accomplishing such methods. Recent studies have indicated that new methods of administering injections may be desirable, particularly for individuals which exhibit impaired hand function, poor motor skills or other such challenges. For example, referring to FIGS. 1A and 1B, according to an independent study of 750 men and women, hand strength generally declines with age (as adapted from a study by entitled Single and Composite Relationships Between Modes of Isometric Force Exertion in Young and Elderly Adults by A. I. M Voorbij and L. P. A Steenbekkers, and published in the book Isometric and Isoinertial Force Exertion in Product Handling by A. I. M Voorbij, pages 68-76, (2000)). As indicated by data curve 102 shown in FIG. 1A, the twisting force exhibited by healthy men declines from nearly 9 Newton-meters (Nm) to approximately 5 Nm as an individual progresses from the age of 25 to the age of 85. Similarly, as indicated by data curve 104 in FIG. 1A, the twisting force exhibited by healthy women declines from approximately 5.5 Nm to approximately 3.5 Nm during the same time period.

Figure 1B:
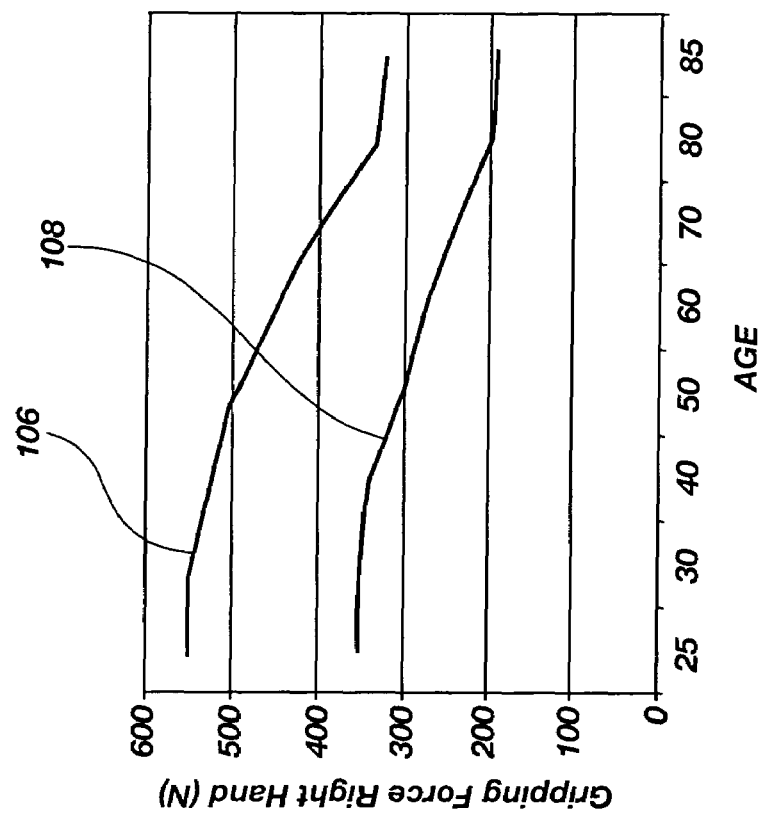
FIGS. 1A and 1B are graphs depicting the twisting strength and gripping strength, respectively, of individuals as a function of age.
Figure 1A:
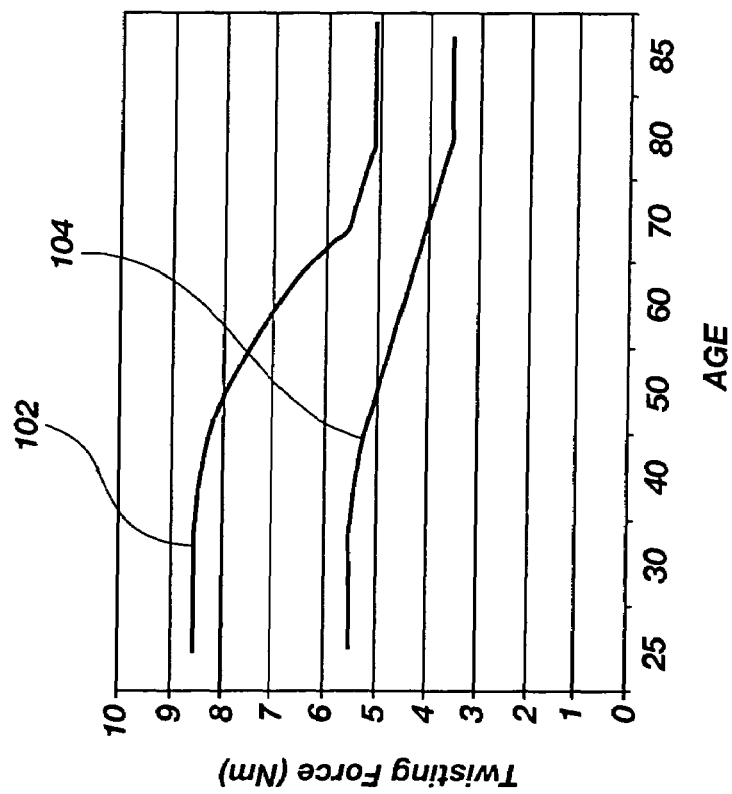

Also, as indicated by data curve 106 shown in FIG. 1B, the gripping force exhibited by healthy men declines from approximately 550 Newtons (N) to a little more than 300 N as an individual progresses from the age of 25 to the age of 85. Similarly as indicated by data curve 108 in FIG. 1B, the gripping force exhibited by healthy women declines from approximately 350 N to a little less than 200 N during the same time period. Generally, it has been determined that healthy women have, on average, approximately 54% of the grip force of healthy men. However, rheumatic women have approximately only 20 to 30% of the grip force of healthy women of similar age. Thus, it becomes clear that elderly individuals and individuals with rheumatoid arthritis or other similar impairments often lack the ability to satisfactorily manipulate complex mechanisms such as conventional injection devices.

Another recent study considered the abilities of elderly individuals and individuals with impaired hand function with regard to their ability to administer therapeutic injections. The study involved twelve individual participants, divided into two groups, wherein the participants simulated injections into their thighs and/or abdomens using dummy models of various injection devices.

The first group of participants included six women ranging from 71 to 83 years in age which had been diagnosed with osteoporosis but which exhibited normal hand and arm function for individuals having the same age. Additionally, although exhibiting relatively normal hand function, the individuals of the first group exhibited some minor disabilities with regard to their hand function. For example, one individual exhibited reduced hand strength, one individual expressed that they had painful wrists, one individual exhibited fatigue in the use of their hands, and one individual exhibited periodic hand tremors.

The second group of participants included five women and one man ranging from 53 to 64 years in age, each of which had been previously diagnosed with osteoporosis and rheumatoid arthritis. The participants of the second group exhibited at least a degree of impaired hand and arm function. More specifically, the participants of the second group exhibited limited strength, mobility and ability to grip objects in their hands, and also experienced pain in their hands and/or arms.

It is noted that at least four participants from the first group had previous experience regarding injection treatments, while at least three participants from the second group had such experience. Additionally, most of the participants were currently utilizing multiple medications (i.e., more than six different medications per person). The participants generally had normal vision for their age which, in most cases, means that they could not read fine print without the assistance of glasses. One of the participants had partial vision.

Figure 2C:
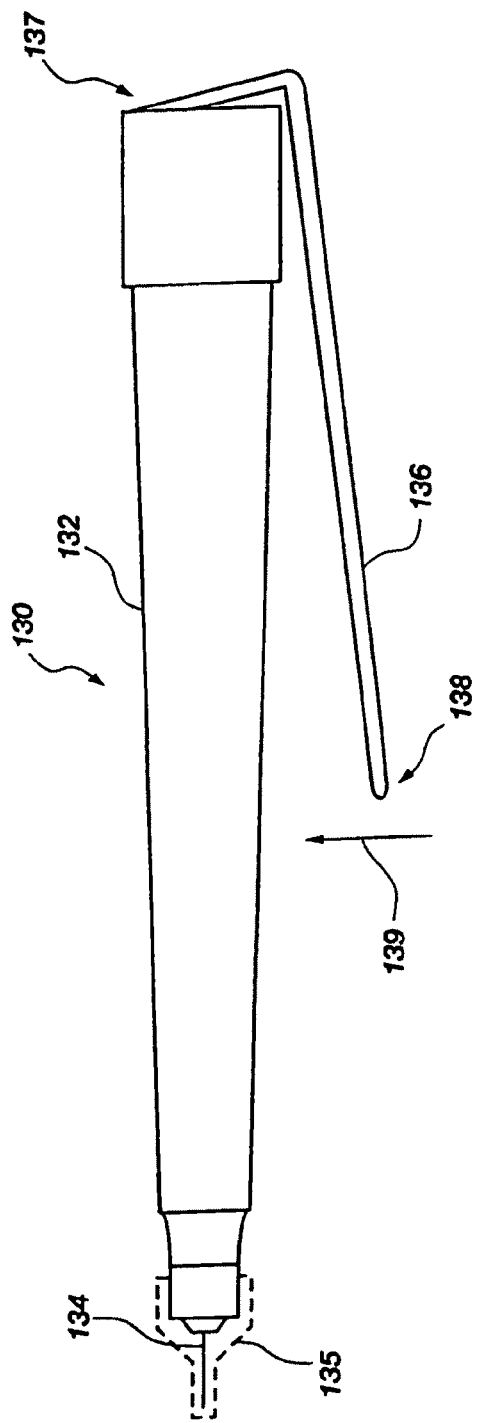

Referring now to FIGS. 2A-2D, exemplary embodiments of injection devices are shown which were utilized during the presently disclosed study. FIG. 2A shows injection device 110 and generally similarly configured injection device 110' with each device 110, 110' being used for different portions of the study. Specifically, the difference between the injection device 110 used in the first portion of the study, and the injection device 110' used in the second portion of the device is the stroke distance 'S' of the actuator 116 and the magnitude of the force required to displace the actuator the specified stroke distance S.

The injection device 110 as used in the first portion of the study generally included a housing 112 having a needle 114 (or, for purposes of simulation, a needle guard 115) at one end thereof and an actuator 116 at a second, opposing end thereof. The actuator 116 was generally configured as a button which was displaceable in the direction of the needle 114. For the first portion of the study, the stroke S of the actuator 116, or the distance which the actuator was required to be displaced in order to effect delivery of fluid product through the needle 114, was approximately 5 millimeters (mm). The force required to completely depress the actuator was approximately 25 to 30 N.

After explaining to the operation of the injection device 110 to the participants of the study, a spontaneous response from an individual in the first group regarding the use of the device 110 included the perception that the actuator 116 looked "pretty hard to press." Spontaneous responses from individuals in the second group included the perception that operation of the device "looks very difficult" and that operation thereof "will be impossible."

Each of the individuals were asked to simulate an injection, in both their thighs and their abdomen, using the injection device 110. It is noted that significantly different wrist angles are required in administering an injection in the thigh as compared to administering an injection in the abdomen. The results of the simulated injections are shown below in TABLE 1 and TABLE 2.

TABLE 1

Group 1; Injection device 110 with 5 mm stroke

| Degree of Difficulty in Operating Device | Number of individuals |
| --- | --- |
| Very Easy | 0 |
| Easy | 2 |
| Neither Easy nor Difficult | 1 |
| Difficult | 2 |
| Very Difficult | 0 |
| Did not Manage Operation | 1 |

TABLE 2

Group 2; Injection device 110 with 5 mm stroke

| Degree of Difficulty in Operating Device | Number of individuals |
| --- | --- |
| Very Easy | 0 |
| Easy | 0 |
| Neither Easy nor Difficult | 0 |
| Difficult | 1 |
| Very Difficult | 1 |
| Did not Manage Operation | 4 |

Comments from individuals of the first group regarding their attempts to operate the device 110 included statements that it was "difficult," "hard to press," requiring a "high force" and that it was "rather uncomfortable."

Comments from individuals of the second group regarding their attempts to operate the device 110 included the following: "Very hard to press, although I'm pretty strong at the moment," "far too hard to press down—all [my] fingers hurt," "[I] would not manage even if I use both hands and press with the entire hand," "[this is] really hard to press—far to hard, even with my best thumb," "not possible due to high force," and "hard to press—not possible with [my] left hand" (the particular individual requiring the right hand for grasping the skin fold). It is noted that, of the combined groups, half of the users either found it very difficult (one individual) or could not manage successful operation of the device (five individuals).

A similar simulation was performed using an injection device—referred to as injection device 110' for purposes of clarity and distinction—configured as shown in FIG. 2A and which exhibited a stroke S of 10 mm and a required force to displace the actuator 116 of approximately 6 to 9 N. Spontaneous reactions of individuals from the second group upon seeing the device 110' included that they could "see it would be impossible" and that the operation of the device "looks very difficult." The results of the simulated injections are shown below in TABLE 3 and TABLE 4.

TABLE 3

Group 1; Injection device 110' with 10 mm stroke

| Degree of Difficulty in Operating Device | Number of individuals |
| --- | --- |
| Very Easy | 2 |
| Easy | 2 |
| Neither Easy nor Difficult | 1 |
| Difficult | 1 |
| Very Difficult | 0 |
| Did not Manage Operation | 0 |

TABLE 4

Group 2; Injection device 110' with 10 mm stroke

| Degree of Difficulty in Operating Device | Number of individuals |
| --- | --- |
| Very Easy | 0 |
| Easy | 1 |
| Neither Easy nor Difficult | 0 |
| Difficult | 3 |
| Very Difficult | 0 |
| Did not Manage Operation | 2 |

Comments from individuals of the first group regarding their attempts to operate the second injection device 110' (with 10 mm displacement) included statements that it was "very easy—much better than [the first injection device 110]," "a bit easier than [the first injection device 110]," "much easier than [the first injection device 110]" and that it "feels awkward—similar to [the first injection device 110]."

Comments from individuals of the second group regarding their attempts to operate the second injection device 110' included the following: "better than [the first injection device 110]," "too much strain for the thumb—feels awkward," "same as [the first injection device 110]—will not be possible," "easier than [the first injection device 110], but too much strain for the thumb—[I] would not like it," "it works, but it's unsteady due to the great effort," and "not possible with [my] left hand" (the particular individual requiring the right hand for the skin fold). It is noted that all but one of the individuals of the second group either found operation of the device to be difficult (three individuals) or could not manage successful operation of the device (two individuals).

Referring to FIG. 2B, an injection device 120 includes a housing 122 having a needle 122 (or, for purposes of simulation, a needle guard 123) at one end thereof and a generally radially projecting actuator 124 proximal a second end thereof. The actuator 124 is configured such that displacement thereof a defined stroke distance S, as indicated by directional arrow 126 and as represented by the dashed lines, activates an appropriate mechanism to dispense a fluid product through the needle 122. Upon seeing the injector device 120 and learning of its operation, at least one individual indicated that such operation "seems awkward." Both groups were asked to simulate injections using the injection device. The results of the simulations are shown in TABLE 5 and TABLE 6.

TABLE 5

Group 1; Injection device 120

| Degree of Difficulty in Operating Device | Number of individuals |
| --- | --- |
| Very Easy | 0 |
| Easy | 2 |
| Neither Easy nor Difficult | 2 |
| Difficult | 2 |
| Very Difficult | 0 |
| Did not Manage Operation | 0 |

TABLE 6

Group 2; Injection device 120

| Degree of Difficulty in Operating Device | Number of individuals |
| --- | --- |
| Very Easy | 1 |
| Easy | 2 |

TABLE 6-continued

Group 2; Injection device 120

| Degree of Difficulty in Operating Device | Number of individuals |
| --- | --- |
| Neither Easy nor Difficult | 1 |
| Difficult | 1 |
| Very Difficult | 0 |
| Did not Manage Operation | 1 |

Regarding the operation of the injection device 120, comments from the first group included the following: "feels a bit awkward—difficult to press with the thumb," "works OK, but not my cup of tea," "really easy, but [the second injection device 110'] is better," "[I] liked [the first and second injection devices 110 and 110'] better—[it's] a strange angle, [I] don't like it," and "[it] might be easier to press slowly."

Referring to FIG. 2B, an injection device 120 includes a housing 122 having a needle 121 (or, for purposes of simulation, a needle guard 123) at one end thereof and a generally radially projecting actuator 124 proximal a second end thereof. The actuator 124 is configured such that displacement thereof a defined stroke distance S, as indicated by directional arrow 126 and as represented by the dashed lines, activates an appropriate mechanism to dispense a fluid product through the needle 121. Upon seeing the injector device 120 and learning of its operation, at least one individual indicated that such operation "seems awkward." Both groups were asked to simulate injections using the injection device. The results of the simulations are shown in TABLE 5 and TABLE 6.

Referring to FIG. 2C, an injection device 130 includes, generally, a housing 132, a needle 134 (or, for purposes of simulation, a needle guard 135) disposed at one end of the housing 132, and an actuator 136 configured generally as a pivoting lever. The actuator 136 is configured such that rotation of the lever about a fulcrum or pivot point 137 to displace the free end 138 thereof towards the housing 132, as indicated by directional arrow 139, operates an appropriate mechanism to dispense a fluid product through the needle 134. Upon showing the injection device and learning of its operation, various individuals made spontaneous comments such as "looks comfortable for the hand," "seems easiest," and "I'm curious of this one—seems easiest." The individuals were asked to simulate injections using the injection device 130. The results of such simulations are set forth in TABLE 7 and TABLE 8.

TABLE 7

Group 1; Injection device 130

| Degree of Difficulty in Operating Device | Number of individuals |
| --- | --- |
| Very Easy | 1 |
| Easy | 3 |
| Neither Easy nor Difficult | 0 |
| Difficult | 2 |
| Very Difficult | 0 |
| Did not Manage Operation | 0 |

TABLE 8

Group 2; Injection device 130

| Degree of Difficulty in Operating Device | Number of individuals |
|---|---|
| Very Easy | 2 |
| Easy | 3 |
| Neither Easy nor Difficult | 0 |
| Difficult | 1 |
| Very Difficult | 0 |
| Did not Manage Operation | 0 |

Regarding operation of the injection device, comments from the first group included the following: "can use my whole hand to press," "may be good, but a bit difficult to find a way to hold it," and "difficult to find a way to hold it."

Comments from the second group included the following: "thought it would be easier—a bit too narrow grip," "easy, handy, not too much strain on any finger," "rather easy," "perfect—very simple, very comfortable," "lever is really good," and "easy, but a bit difficult to hold still" (also noting that it works better after some training). It is noted that, while three individuals found the injection device 130 to be difficult to operate, all of the individuals were able to manage operation of the injection device and three-fourths of the individuals found it either easy to use (six individuals) or very easy to use (three individuals).

Figure 2D:
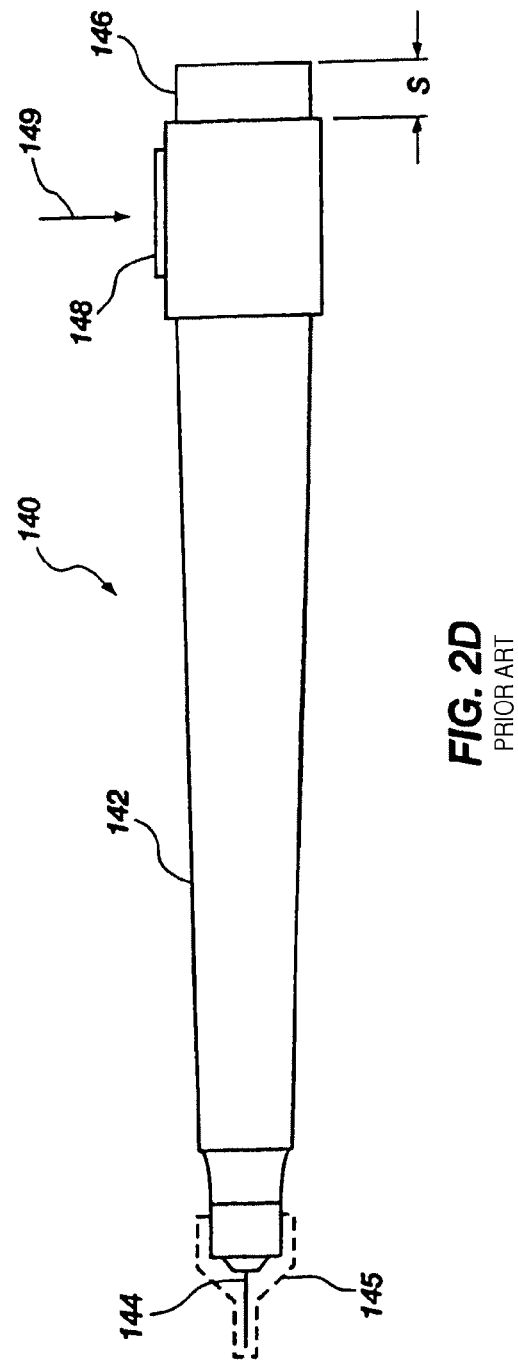

Referring now to FIG. 2D, an injection device 140 includes, generally, a housing 142, a needle 144 (or, for purposes of simulation, a needle guard 145) disposed at one end of the housing 142, a preloading actuator 146 and a release or delivery actuator 148. The preload actuator 146 is configured to be displaced in the direction of the needle 144 a specified stroke distance S.

Initial actuation of the preload actuator 146 does not cause delivery of a fluid product through the needle 144 but, instead stores energy with respect an associated mechanism (preloads the mechanism) such that, when the release actuator 148 is operated by depressing it as indicated by directional arrow 149, the preloaded mechanism effects delivery of a fluid product through the needle 144. Thus, the preload actuator 146 may be, and desirably is, displaced prior to insertion of the needle 144 into a user's skin. Upon insertion into a user's skin, the release actuator 148 may be pressed with nominal effort to release the stored energy and effect delivery of a fluid product through the needle 144.

Upon showing the injection device and learning of its operation, various individuals made spontaneous comments such as "[I] like the idea." The results of such simulations are set forth in TABLE 9 and TABLE 10.

TABLE 9

Group 1; Injection device 140

| Degree of Difficulty in Operating Device | Number of individuals |
|---|---|
| Very Easy | 2 |
| Easy | 4 |
| Neither Easy nor Difficult | 0 |
| Difficult | 0 |
| Very Difficult | 0 |
| Did not Manage Operation | 0 |

TABLE 10

Group 2; Injection device 140

| Degree of Difficulty in Operating Device | Number of individuals |
|---|---|
| Very Easy | 5 |
| Easy | 1 |
| Neither Easy nor Difficult | 0 |
| Difficult | 0 |
| Very Difficult | 0 |
| Did not Manage Operation | 0 |

Regarding operation of the injection device, comments from the first group included the following: "[I] don't know— [it's] easy to use but hard to understand," "[it's] handy, eliminates the need to think," "[you have] to learn how to do it, but once you that it is easy," "rather good—[it's] good not to have to press for several seconds," and "comfortable in the hand—a bit funny."

Comments from the second group included the following: "[it's] awkward on the side—I'm used to the button on the top," "very easy," "easiest," and "[it's] hard to load but easy to release—it is the best one." It is noted that, all of the participants managed successful operation of the device and all found its use to be either easy (5 participants) or very each (7 participants).

After considering the results of the above-disclosed study, it was determined that a new method of administering injections and a new injection device should be provided that would make it simpler for individuals, including elderly users, those with impaired hand functions, reduced hand strength or deteriorated motor skills, to administer such injections.

Figure 3:
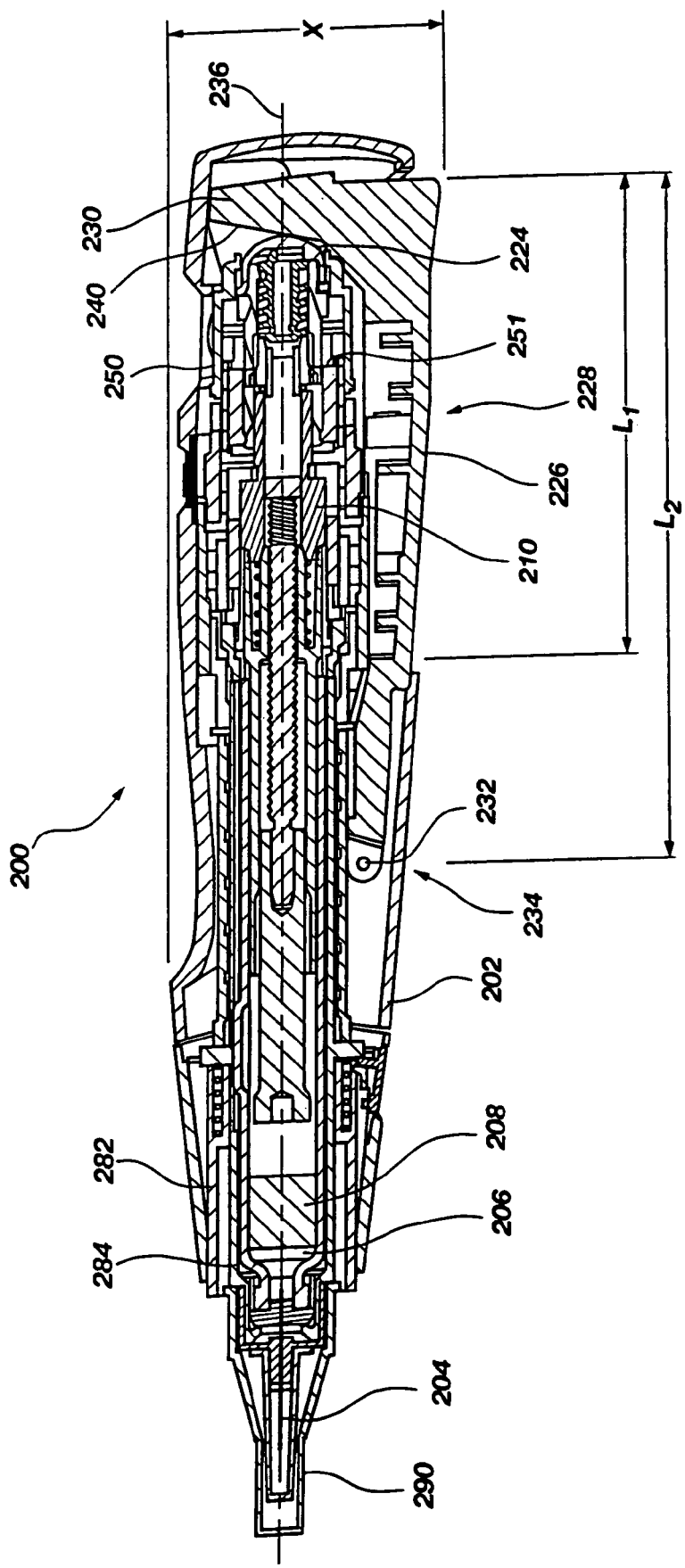
FIG. 3 is a cross-sectional view of an injection device in accordance with an embodiment of the present invention.
Figure 4:
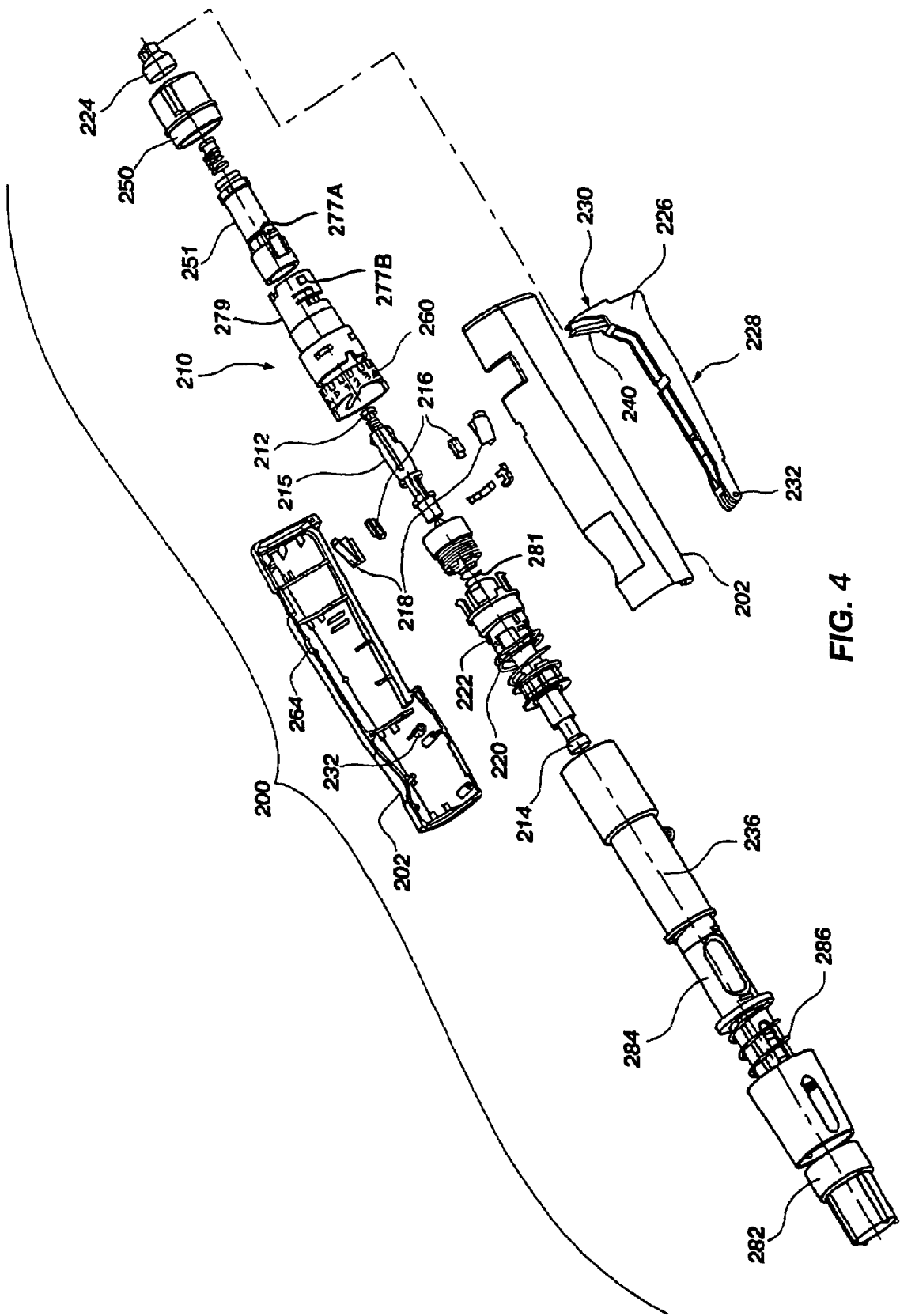
FIG. 4 is an exploded view of the injection device shown in FIG. 3.

One such exemplary injection device 200 is shown in FIGS. 3 and 4. The exemplary injection device 200 includes a casing or housing 202 in which are disposed various mechanisms and apparatuses. For example, an injection needle 204, configured as a cannula to effect delivery of a fluid product therethrough, is coupled with the housing 202 and is placed in fluid communication with the contents of a product container 206, which may also be referred to as a cartridge, a carpoule, or an ampoule. A piston 208 is disposed within the product container 206 and is displaceable therein. A dispensing mechanism 210 is configured to contact and exert a force on the piston 208 such that, upon displacement of the piston 208 within the product container 206, the fluid product contained therein is forced through the injection needle 204. The dispensing mechanism 210 includes a threaded drive rod 212 (which may also be called a piston rod) that is coupled to a flanged end 214 configured to contact and displace the piston 208. The dispensing mechanism 210 further includes a piston rod sleeve 215 and a split nut assembly, including a split nut 216, a split nut slider 218, a split nut spring 220 and spring holder 222. The dispensing mechanism 210 may further include a cap 224, which in turn may include a rounded end or any other suitable configuration for interaction with an actuating lever 226.

The actuating lever 226 interacts with the dispensing mechanism 210 of the injection device 200 and includes an arm 228 that extends generally longitudinally (or at a small angle) with respect to the housing 202, and a protrusion 230 that extends generally radially inwardly from the arm 228 and with respect to the housing 202. The lever 226 is configured to rotate about a pivot or fulcrum 232. The fulcrum 232 is located at the end of the lever 226 opposite that of the laterally extending protrusion 230 and is fixed relative to the housing 202. In one exemplary embodiment, the fulcrum 232 is positioned at a location which is substantially along, or immediately adjacent, the circumferential surface 234 of the injection device 200. The lever 226 is, thus, capable of being pivotally displaced about the fulcrum 232 relative to the housing 202. Such a pivoting motion enables the lever 226 to be moved towards and away from the longitudinal axis 236 of the injection device 200. The lever arm 228 provides a surface area for engagement by a user which, in one embodiment, desirably exhibits a length corresponding to the average width of a specified number of fingers, as discussed in further detail below.

As noted above, the protrusion 230 of the lever 226 extends substantially radially from the lever arm 226 into the housing 202 at an end of the injection device 200 opposite the needle 204. An interfacing surface 240 of the protrusion 230, which generally faces the threaded drive rod 212, may exhibit an oblique angle with respect to a longitudinal axis 236 of the housing 202 and is configured to act as an inclined plane with respect to the cap 224 of the dispensing mechanism 210. Thus, the interfacing surface 240 interacts with the cap 224 to cause the displacement thereof upon rotation or pivoting of the lever 226 about the fulcrum 232.

Figure 5A:
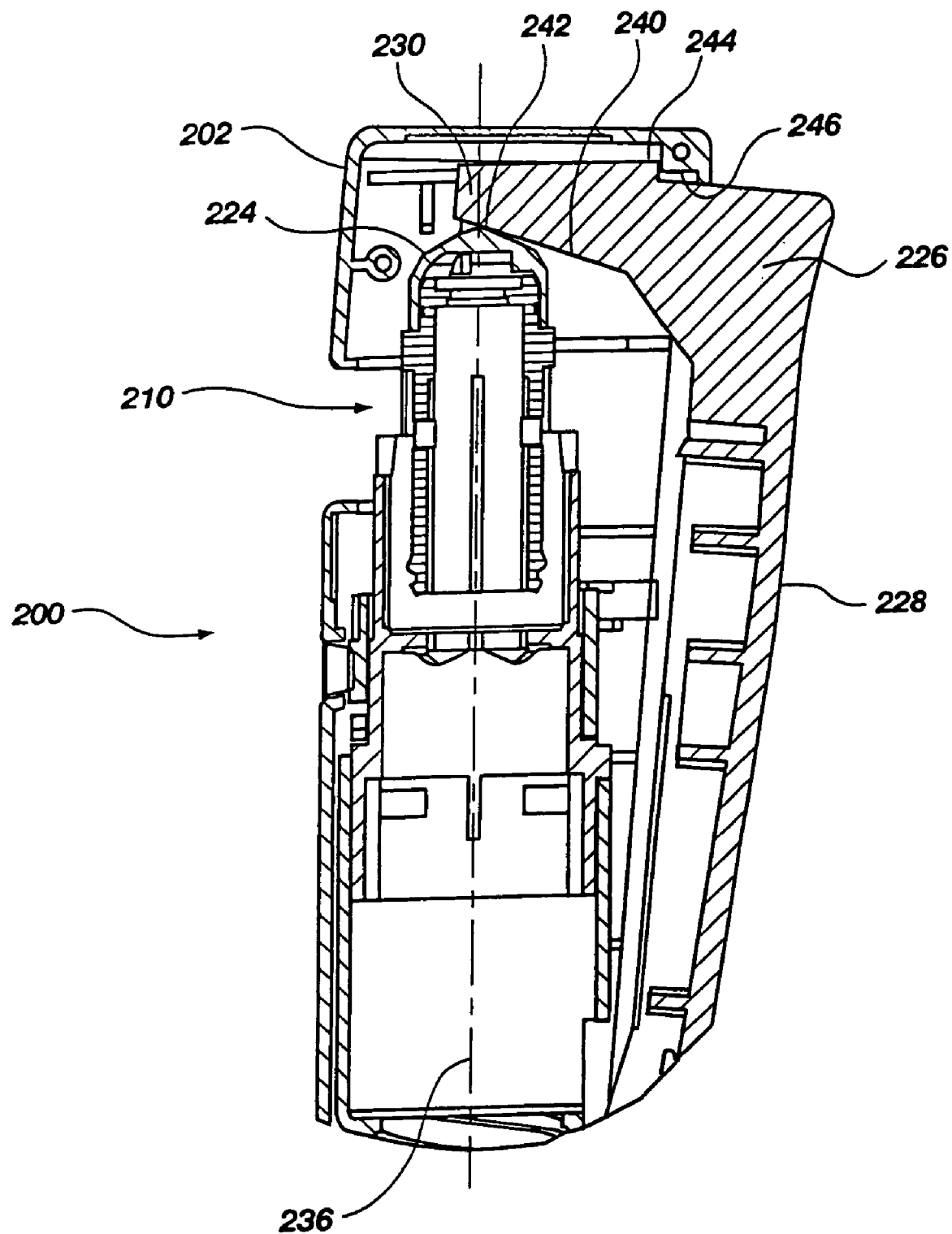
FIGS. 5A and 5B are cross-sectional views of an actuator of the device of FIG. 3 with the actuator in a first position and a second position, respectively.

Referring briefly to FIG. 5A, an enlarged cross-sectional view is shown of a portion of the injection device 200, including the interfacing surface 240 of the actuator lever 226. FIG. 5A shows the lever 226 in a first state or position wherein the lever arm 228 is in a retracted position or, in other words, when it is pivoted generally radially outward and away from the housing 202 of the injection device 200. The point of interface, referred to herein as the contact point 242 between the interfacing surface 240 of the protrusion 230 and the cap 224 of the dispensing mechanism 210, is generally towards an end of the protrusion 230, which is distal relative to the arm 228 of the lever 226 when the lever 226 is in the first state or position. The position or state illustrated in FIG. 5A shows the injection device 200 in what may be termed a starting position or, in other words, in a position prior to dispensing a desired volume of the fluid product from the product container 206.

A stepped surface 244 may be formed along another surface of the protrusion 230, opposite the interfacing surface 240. The stepped surface 244 may cooperatively interfere with a shoulder 246 formed in the housing 202 to prevent the lever 226 from pivoting outwardly relative to the longitudinal axis 236 beyond a desired position.

Figure 5B:
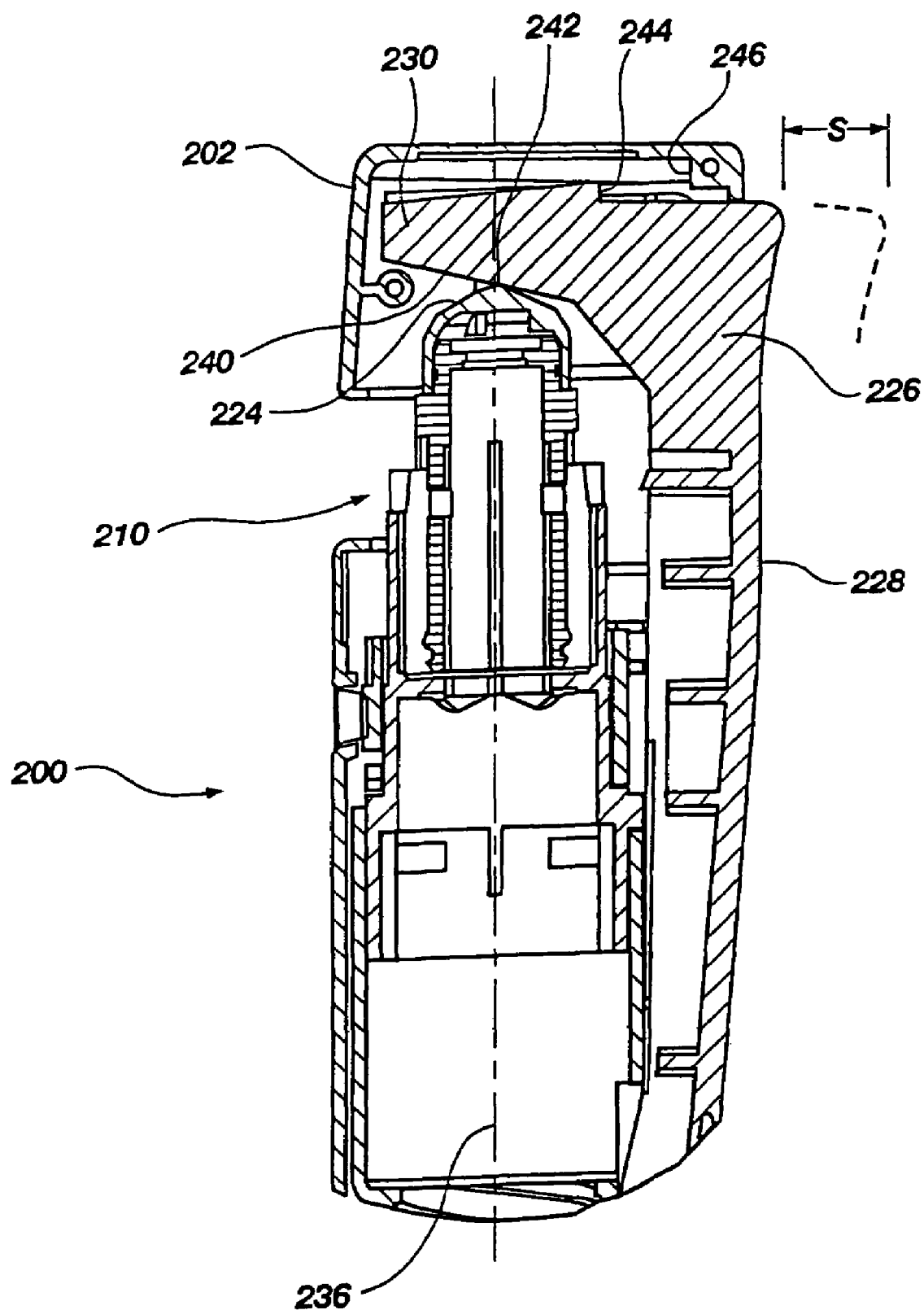

Referring now to FIG. 5B, an enlarged cross-sectional view of the injection device 200 is shown in a second state or position, wherein the lever 226 is pivoted or pushed in the radial direction generally towards the longitudinal axis 236 such that its arm 228 is contracted relative to the housing 202. With the lever 226 in this position, the contact point 242 between the interfacing surface 240 of the protrusion 230 and the cap 224 of the dispensing mechanism 210 now lies further along the interfacing surface 240 towards the arm 228 of the lever 226. Upon rotation of the lever 226 from the first position (FIG. 5A) to the second position (FIG. 5B), the interfacing surface 240 acts as an inclined plane which exerts a force on the cap 224 in the direction of the needle 204 (FIGS. 3 and 4) and along the longitudinal axis 236.

Thus, referring to FIGS. 3 through 5B, when the lever 226 is pivoted about the fulcrum 232 from the first position (FIG. 5A) to the second position (FIG. 5B), the contact point 242 changes its position along the interfacing surface 240 of the protrusion 230, which surface is angled relative to the longitudinal axis 236 and, thus, converts the generally radial displacement of the protrusion 230 into a force component in a direction along the longitudinal axis 236. This force component displaces the cap 224 and, when properly activated, causes the dispensing mechanism 210 to displace the flanged end 214 of the threaded rod 212, ultimately displacing the plunger 208 a desired distance and expelling a specified volume of fluid product from the product container 206 through the needle 204.

Figure 6:
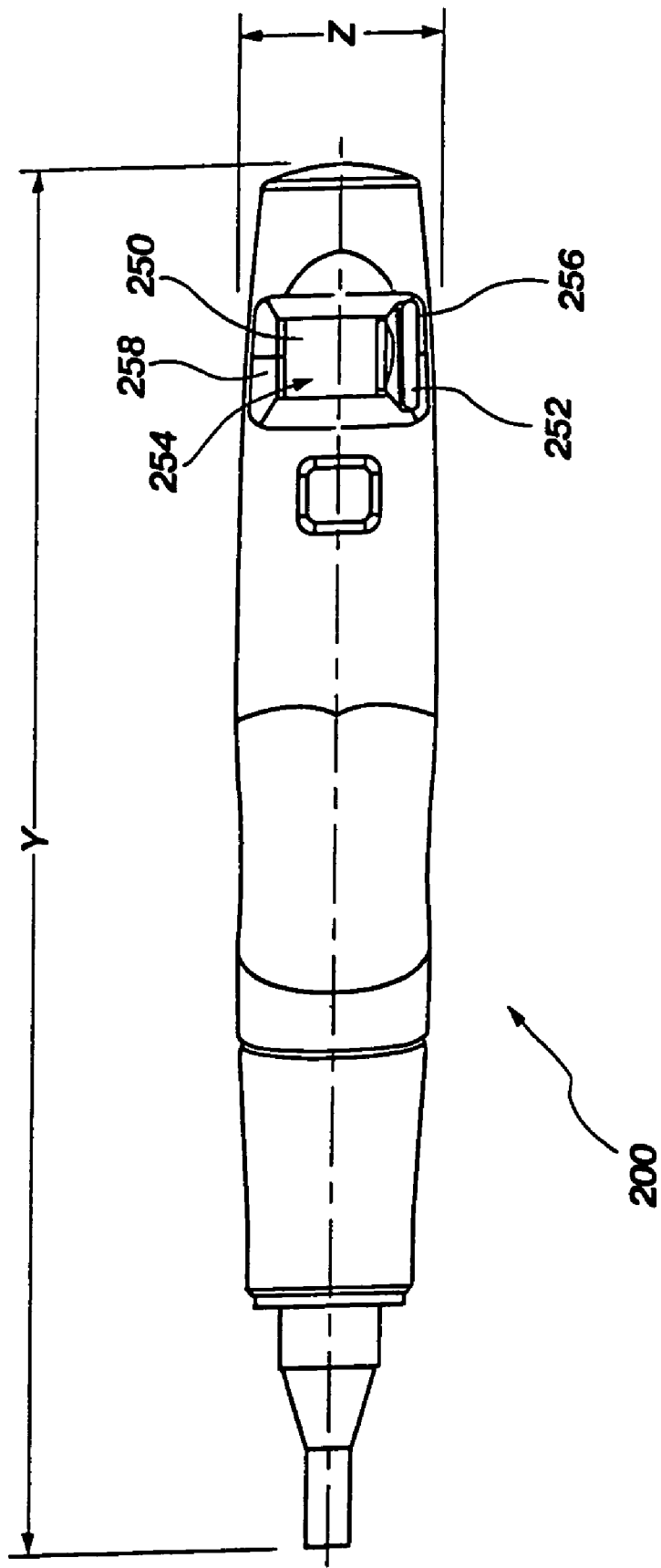
FIG. 6 is a side view of an injection device in accordance with an embodiment of the present invention.

Referring now to FIG. 6 in conjunction with FIGS. 3 and 4, an activating member 250 may be provided in order to effect actuation of the dispensing mechanism 210 upon a displacement of the lever 226 from the first position (FIG. 5A) to the second position (FIG. 5B). The activation member 250 may also act as a safety mechanism to prevent disposal of fluid product through the needle 204 upon inadvertent displacement of the lever 226.

In one embodiment, the activating member 250 may work in cooperation with a coupling sleeve 251 which, in turn, may cooperate with the piston rod sleeve 215, the split nut 216 and split nut sleeve 218 to effect an incremental advancement of the threaded piston rod 212 upon each actuation of the lever 226. The activating member 250 may include a protrusion 252 extending through an opening 254 in the housing 202 which protrusion 252 is displaceable by a user of the injection device 200 between a first position, wherein the protrusion 252 substantially abuts a first edge 256 of the opening 254, and a second position, wherein the protrusion 252 substantially abuts a second opposing edge 258 of the opening 254.

In one embodiment, in an initial setting where the injection device 200 is prepared for administration of an injection, the protrusion 252 is positioned against the second edge 258 and, upon actuation of the lever 226, the cap 224 is displaced in a direction along the longitudinal axis 236 and towards the injection needle 204. Displacement of the cap 224 results in an associated displacement of the coupling sleeve 251, piston rod sleeve 215, split nut 216 and threaded piston rod 212 with its associated flanged end 214. As previously mentioned, actuation of the lever 226 results in a displacement of the flanged end 214 of the threaded rod 214 from an initial position (referred to hereinafter as "position A" for purposes of discussion and clarity) to a second position (referred to hereinafter as "position B") that is closer to the injection needle 204 along the longitudinal axis 236 than is position A.

The displacement of the coupling sleeve 251 causes a biased finger member 277A to engage and interlock with an associated opening 277B formed in a collar 279. The coupling sleeve 251 remains in this locked position until the activating member 250 is displaced such that the protrusion 252 is positioned against the first edge 256 of the opening 254. Upon this displacement of the activating member 250, an internal catch mechanism (not shown) presses the biased finger member 277A to release it from its associated opening 277B. A biasing member, such as a spring 281, causes the piston rod sleeve 215, the split nut 216, the threaded piston rod 212 and the coupling sleeve 251 to be displaced back along the longitudinal axis 236 away from the injection needle 204. It is noted that this displacement of components results in the flanged end 214 being displaced from position B back to position A.

The displacement of the coupling sleeve 251 away from the injection needle 204 also results in a keyed engagement of the coupling sleeve 251 with the activating member 250. Thus, upon subsequent displacement of the protrusion 252 of the activating member 250 from the first edge 256 back to the second edge 258 of the opening 254, the coupling sleeve 251 is rotated about the longitudinal axis 236 through a predetermined angle of rotation relative to the housing 202. Rotation of the coupling sleeve 251 further results in a corresponding rotation the piston rod sleeve 215, the split nut 216 and the split nut sliders 218. However, the threaded piston rod 212 is installed such that it is not permitted to rotate about the longitudinal axis 236 relative to the housing 202. Thus, upon rotation of the piston rod sleeve 215 and split nut 216 (as effected by the displacement of the activating member discussed hereinabove), the threaded coupling formed between the split nut 216 and the threaded piston rod 212 results in the displacement of the threaded piston rod 212 along the longitudinal axis 236 in the direction of the injection needle 204. In essence, rotation of the piston rod sleeve 215 and split nut 216 relative to the threaded piston rod 212 results in the displacement of the flanged end 214 from position A back again to position B. It is noted that, since the flanged end 214 has already been advanced to position B, the advancement effected by the rotation of the piston rod sleeve 215 and split nut 216 does not result in further advancement of the piston 208 within the product container. The injection device 200 is now activated and ready for administration of another injection.

Upon actuation of the lever 226 during a subsequent injection, the various components interact as described hereinabove such that the flanged end 214 of the threaded piston rod 212 is advanced from position B to another position (which might be termed "position C") along the longitudinal axis 236 towards the injection needle 204. The previously described series of events regarding displacement of the activating member 250 and the consequential displacement of related components may be repeated, resulting in the sequential and cumulative incremental advancement of the flanged end 214 of the threaded piston rod 212 through a series of positions along the longitudinal axis 236 in the direction towards the injection needle 204 (i.e., from position A, to position B, eventually to position C, etc.).

It is noted that, with the protrusion 252 positioned against the first edge 256 of the opening 254, displacement of the lever 226 does not result in advancement of the flanged end 214 of the threaded drive rod 212 to a longitudinal position that would result in expulsion of any product from the product container 206. Instead, repeated displacement of the lever 226 while the protrusion 252 is positioned against the first edge 256 will simply result in the cycling of the flanged end 214 between two previously attained positions (e.g., between position B and position C assuming that position C was the furthestmost longitudinal position attained by the flanged end 214).

It is further noted that the activating member 250 may be configured such that it shows a first indicia through the opening 254 when the protrusion 252 is positioned against the first edge of the opening 254 and a second indicia when the protrusion is positioned against the second edge 258 of the opening. By viewing the indicia present on the activating member 250, a user will be able to more readily determine the position of the activating member 250 and whether they need to reposition the activating member 250 prior to displacing the lever 226. Such indicia may include letters, numbers, colors or other symbols as may be appropriate.

After the threaded piston rod 212 has been advanced to its maximum longitudinal position (such as when all of the contents of the product container 206 have been expelled therefrom) an appropriate mechanism may allow the split nut 216 to release from the threaded piston rod 212 so that it may freely slide back to its initial position (e.g., back to position A). Once the threaded piston rod 212 is back to its initial position, the mechanism may cause the split nut 216 to reengage the threaded piston rod 212 such that it may be incrementally advanced in the manner previously described. One such mechanism is disclosed in PCT Publication WO 2004/002556A1, entitled "Product Distribution Device With Rapid Piston Resetting," although other mechanisms are known in the art and may be used.

It is also noted that other internal mechanisms and assemblies may be utilized to effect the consistent incremental advance of the threaded piston rod 212. For example, in another embodiment, displacement of the activating member 250 may result in the engagement and disengagement of the split nut 216 with the threaded piston rod 212. In such an embodiment, with the protrusion 252 positioned against the first edge 256 of the opening 254, displacement of the lever 226 does not result in actuation of the dispensing mechanism 210. However, with the protrusion 252 positioned against the second edge 258 of the opening 254, the activating member 250 may act on an appropriate mechanism so as to cause engagement of the split nut 216 with the threaded piston rod 212. Subsequent displacement of the lever 226 may then cause the threaded rod 212 to be displaced a predetermined distance along the longitudinal axis 236.

Additionally, in one embodiment, upon displacement of the lever 226, the activating member 250 may also be automatically and concurrently rotationally displaced such that protrusion 252 is positioned back against the first edge 256 of the opening 254. In such an embodiment, rotational displacement of the activating member may result, for example, in the disengagement of the split nut 216 from the threaded piston rod 212. Such disengagement would prevent actuation of the dispensing mechanism 210 until the activation member 250 is displaced by the user to position the protrusion 252 against the second edge 258. This resetting of the activation member 250 may result in the longitudinal repositioning of the piston rod sleeve 215 relative to the threaded piston rod 212 and the subsequent reengagement of the split nut 216 with the threaded piston rod 212. The lever 226 may then be actuated and the process repeated to effect the advancement of the threaded piston rod 212 in increments of a predetermined distance.

Regardless of type of advancing mechanism used, advancement of the threaded piston rod 212 to a predetermined distance towards the injection needle 204 enables a consistent volume of fluid product to be dispensed upon each actuation thereof. For example, in one embodiment, the delivery of parathyroid hormone (PTH) may include the consistent delivery of approximately 71 microliters (μl) of PTH upon each actuation of the lever 226 and associated dispensing mechanism 210. Of course, the injection device 200 may be configured to deliver other volumes of fluid product depending, for example, on the contents of the fluid being delivered or other specifics related to a prescribed injection therapy. The amount of fluid being dispensed in each injection is determined, largely, by the relationship of the various internal components including, for example, the pitch and lead angle of the threads on the threaded piston rod 212. Again, it is noted that, in the presently disclosed embodiment, the volume to be delivered is fixed and, thus, is not adjustable by a user of a given injection device 200, but must be adjusted by replacement or rearrangement of internal components associated with the lever 226 and dispensing mechanism 210.

It is noted that other various features may also be incorporated into the injection device. For example, in one embodiment, the injection device 200 may be configured such that, upon displacement of the lever 226 from the first position (FIG. 5A) to the second position (FIG. 5B), the lever 226 is retained in the second position by an appropriate latch, lock or other mechanism configured to operate in association with the activating member 250. The lever 226 thus remains in the second position until the activating member 250 is moved such that the protrusion 252 is displaced from the first edge 256 to the second edge 258, also effecting the release of the lever 226 back to the first position. Retention of the lever 226 in the second position allows a user to apply a force to the lever 226 for a relatively short period of time in order to administer an injection. In other words, a force need only be applied long enough to accomplish displacement of the lever 226 to the second position without having to apply a maintaining force to the lever 226 at the second position for any particular period of time.

Figure 7:
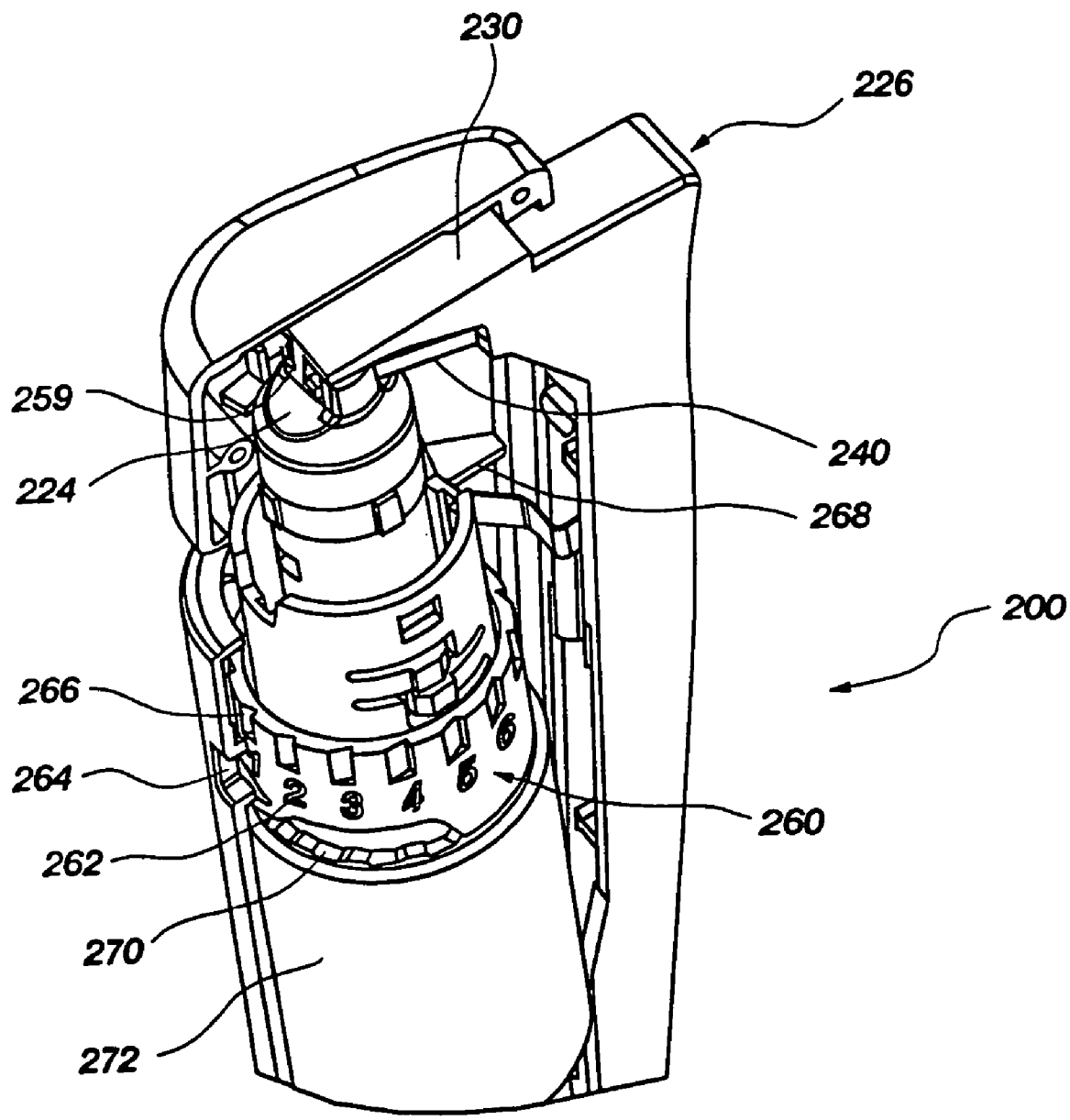
FIG. 7 is a perspective, partial cross-sectional view of a portion of the injection device according to an embodiment of the present invention.

Referring now to FIG. 7, the injection device 200 may include cooperatively mating structures between the lever 226 and the cap 224 of the dispensing mechanism 210. For example, the interfacing surface 240 of the protrusion 230 may include a keyed element 259 such as a T-shaped cross-sectional geometry which slidingly interconnects with a geometrically mating structure on the cap 230 of the dispensing mechanism 210. Such cooperatively mating structures ensure continual engagement of the protrusion 230 of the lever 226 with the cap 224 of the dispensing mechanism.

Additionally, as shown in FIG. 7, and referring also to FIGS. 3 and 4, an indicator 260 may be provided for indicating a remaining or residual product amount within the product container 206. In one embodiment, the indicator 260 may be formed as a rotary scale 262, a portion of which is visible through a window or opening 264 formed in the housing 202. The rotary scale 262 may include a plurality of indicia displayed about its periphery such as, for example, numbers or days of the week, which help a user to determine the number of times they may use the injection device prior to replacing the product container 206. For example, in one embodiment, the rotary scale 262 may include a gradation of whole numbers, each number representing a number of remaining injections available.

In one embodiment, a plurality of notches or serrations 266 are provided on an exterior circumferential surface of the rotary scale 262. An arm 268 associated with the lever 226 extends radially and inwardly therefrom, and substantially tangent to the circumference of the rotary scale 262. The arm 268 is configured to engage one or more of the serrations 266. Additionally, a cooperative ratchet mechanism 270 is formed between the rotary scale 262 and an axially adjacent sleeve 272. The ratchet mechanism 270 enables the rotary scale 262 to rotate in a first direction (e.g., counter clockwise) relative to the sleeve 272 while preventing rotation of the rotary scale 262 in the opposite direction (e.g., clockwise).

Figure 8B:
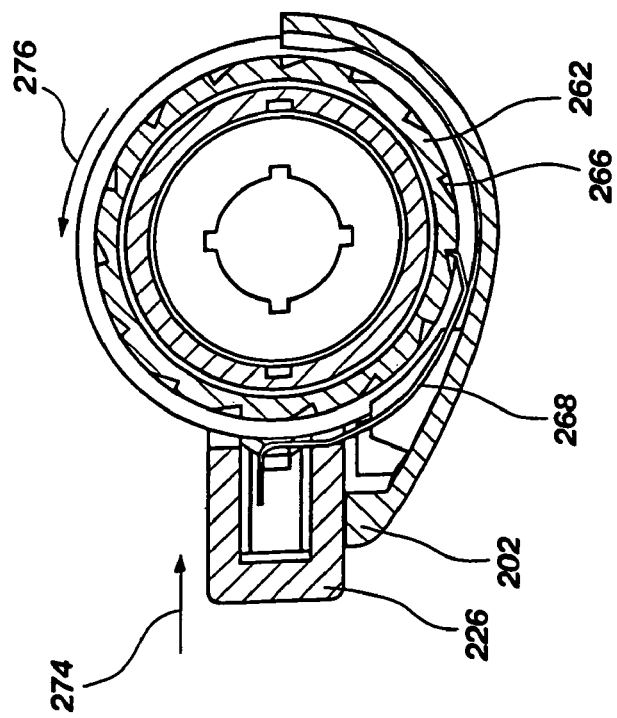
FIGS. 8A and 8B are cross-sectional views of an injection device according to an embodiment of the present invention as indicated in FIGS. 5A and 5B respectively.
Figure 8A:
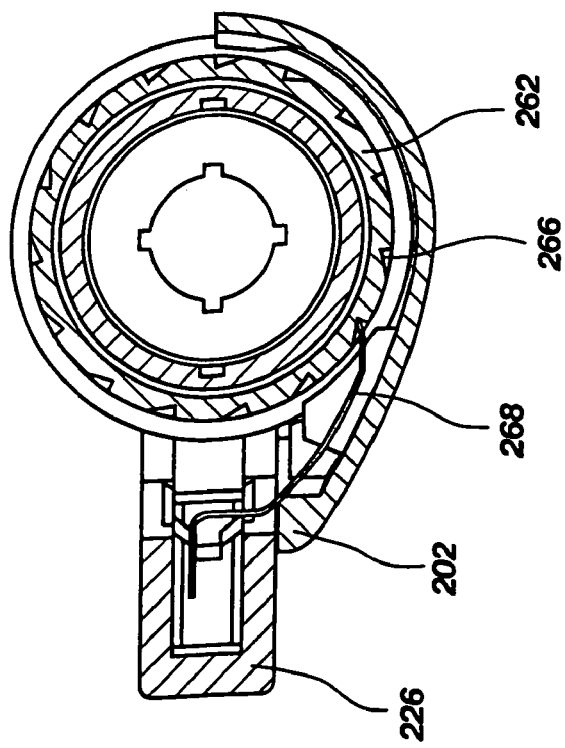

Referring to FIGS. 8A and 8B, operation of a particular embodiment is described. As shown in FIG. 8A, the lever 226 of the injection device 200 is in a first position in preparation for administering an injection of fluid product. More particularly, the lever 226 is in a position generally pivoted away from the housing 202 such as described with respect to FIG. 5A. The arm 268 is engaged with one or more serrations 266 of the rotary scale 262. As shown in FIG. 8B, when the lever 226 is displaced inwardly to the second position (i.e., to the position shown in FIG. 5B) as indicated by directional arrow 274, the arm 268 is likewise displaced. Due to the engagement of the arm 268 with one or more serrations 266, the displacement of the arm 268 causes the displacement of the rotary scale 262 through a specified degree or angle of rotation as indicated by directional arrow 276. Rotation of the rotary scale 262 causes a new indicia (e.g., a new number) to be displayed in the opening or window 264.

In one embodiment, each displacement of the rotary scale 262, as effected by actuation of the lever 226, may result in the display of a whole number. Upon each actuation of the lever 226 which effects the dispensing of a volume of fluid, the scale may "count down" the number of injections remaining based on the known volume of fluid contained in a product container 206 (FIG. 3). In other embodiments, the scale may exhibit the day of the week to remind the user whether or not an injection has been performed on a given day. Of course, other indicia and other indicating schemes may be utilized as will be appreciated by those of ordinary skill in the art.

Figure 9A:
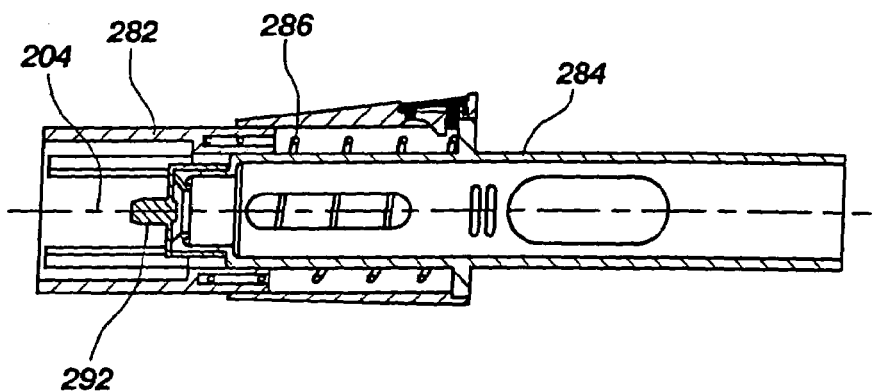
FIGS. 9A-9C are partial cross-sectional views of an injection device including a needle protection apparatus at various positions in accordance with an embodiment of the present invention.
Figure 9B:
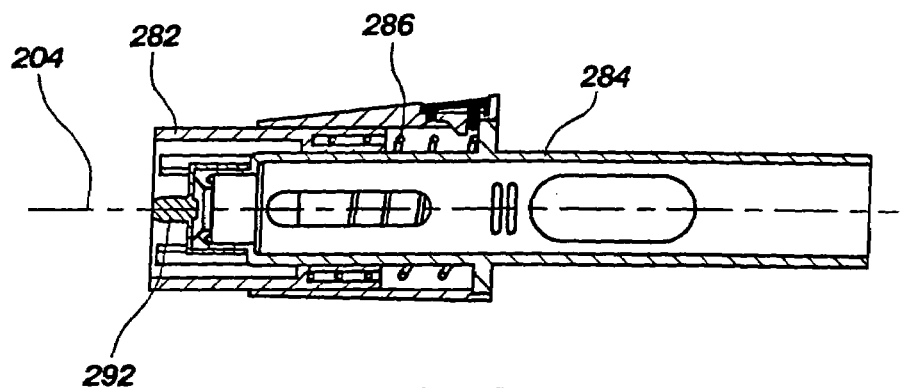
Figure 9C:
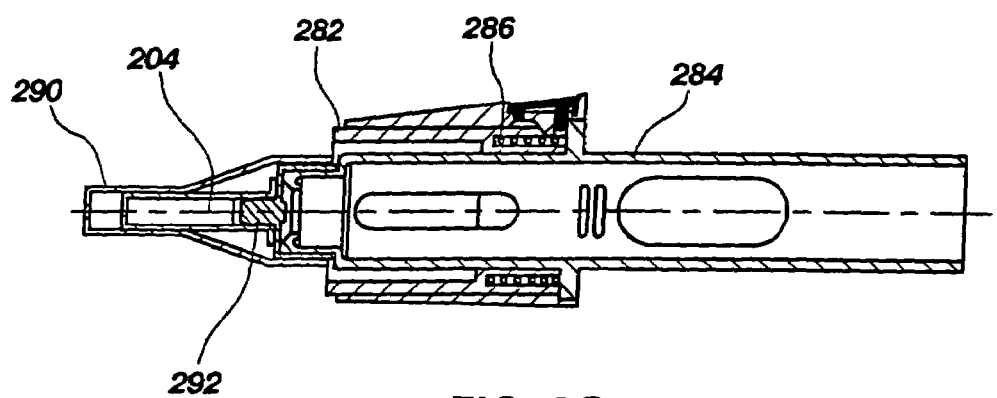

Referring now to FIGS. 9A-9C in conjunction with FIGS. 3 and 4, a needle protection device 280 is shown which may be used in accordance with an embodiment of the present invention. The needle protection device 280 may include a sleeve 282 which is displaceable in a direction generally along the longitudinal axis 236. The sleeve 282 may be slidably coupled with, for example, a cartridge holder 284 configured to receive the product container 206 therein and also configured for attachment to a lower portion of the housing 202. As shown in FIG. 9A, prior to (and after) an injection, the sleeve 282 may be in a longitudinally extended position that completely surrounds the injection needle 204 in the radial direction relative to the longitudinal axis 236.

The cartridge holder 284, together with the sleeve 282, may be configured to be removed and inserted into the housing 202 of the injection device 210 as a unit to accommodate the removal and replacement of product containers 206. With such a configuration, the injection needle 204 may remain protected by the sleeve 282 during the process of exchanging product containers 206. The sleeve 282 may be held in the longitudinally extended position by a biasing member such as, for example, a coiled spring 286. However, as shown in FIG. 9B, the sleeve 282 may be displaced to a retracted position such that the injection needle 204 is exposed by application of an appropriate force to the sleeve 282 relative to the cartridge holder 284. For example, during operation of the injection device 200, the sleeve 282 may be placed in an abutting relationship with a user's skin. Subsequent application of force to the injection device 200 in the direction of the needle 204 generally along the longitudinal axis 236 causes displacement of the sleeve 282 and insertion of the needle 204 into the user's skin. When the injection needle 204 is removed from the user's skin, the sleeve 282 returns to the extended position (FIG. 9A) by virtue of the coiled spring 286. The injection needle 204, therefore, remains substantially protected by the sleeve 282 from exterior access during the entire injection process.

When the injection needle 204 is to be replaced for a subsequent injection, a needle cap 290 may be placed onto the opening of the sleeve 282 as shown in FIG. 9C. When the needle cap 290 is pushed in the direction along the longitudinal axis 236 onto the injection device 200, the sleeve 282 may serve as a guide for placing the needle cap 290 onto the injection needle 204. The injection needle 204, together with the needle cap 290, may then be removed from the injection device 290. A new injection needle 204, already disposed within another needle cap 290, may subsequently be attached to the sleeve 282 and guided towards the cartridge holder 284 for coupling therewith. Such coupling may be accomplished, for example, by a threaded connection or a twist lock between a needle housing 292 and the cartridge holder 284. The needle cap 290 may then be removed and the sleeve returned to an extended position (FIG. 9A). During such a process, a user remains protected from inadvertent needle pricks by virtue of the needle cap 290 and the sleeve 282 that shields the needle 204.

Figure 10A:
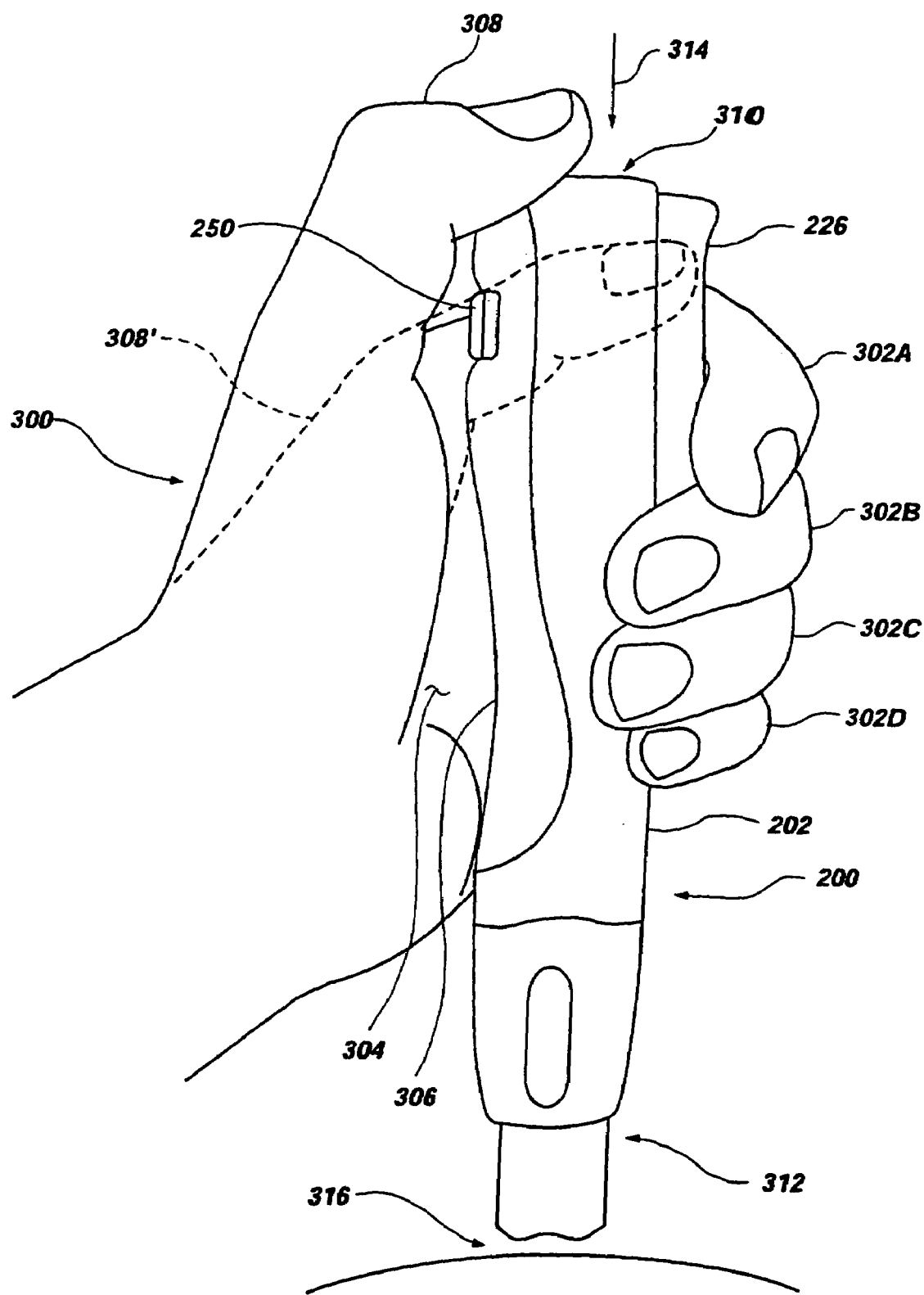
FIGS. 10A-10C depict the use of an injection device in accordance with an embodiment of the present invention.
Figure 10B:
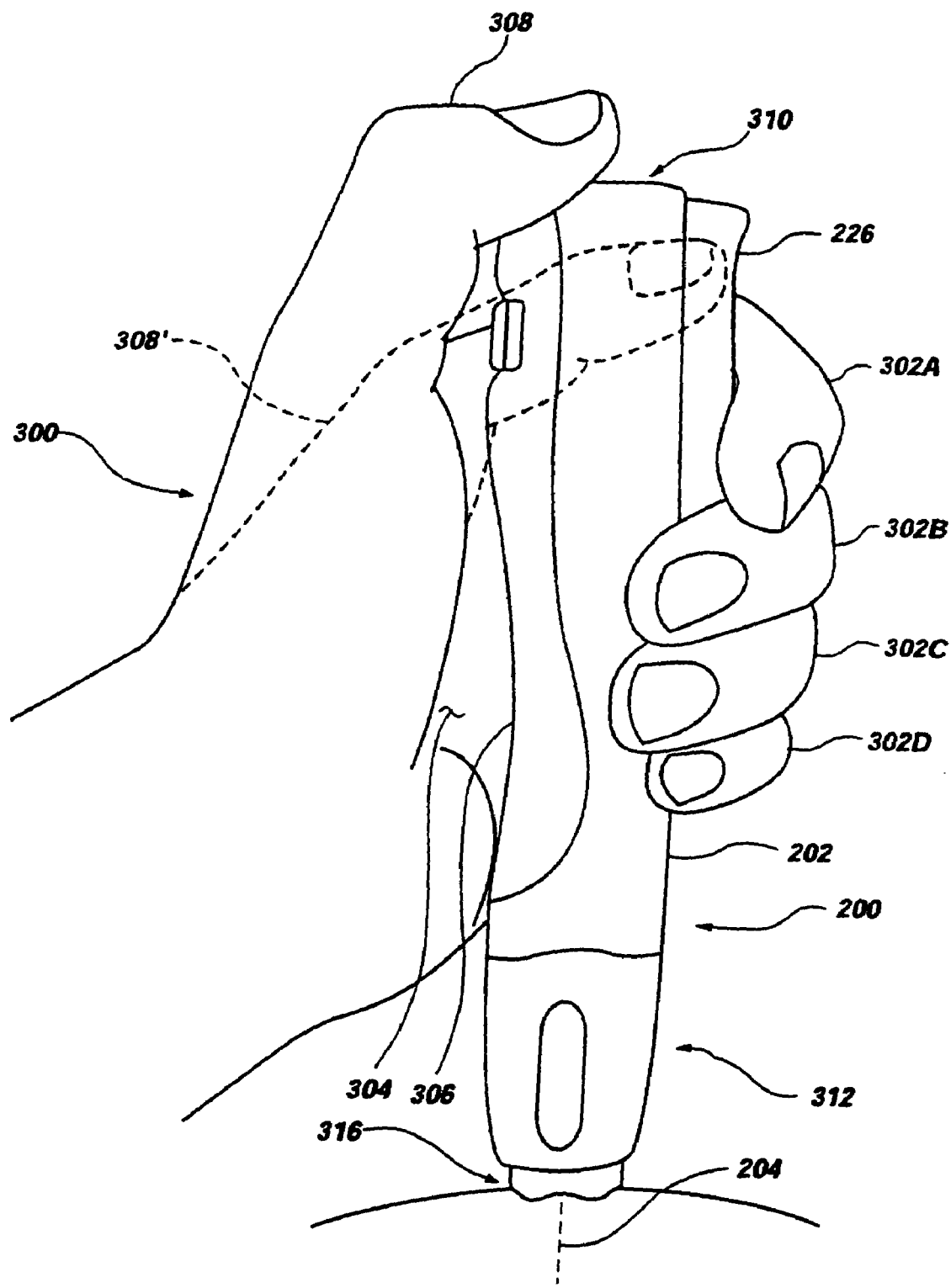
Figure 10C:
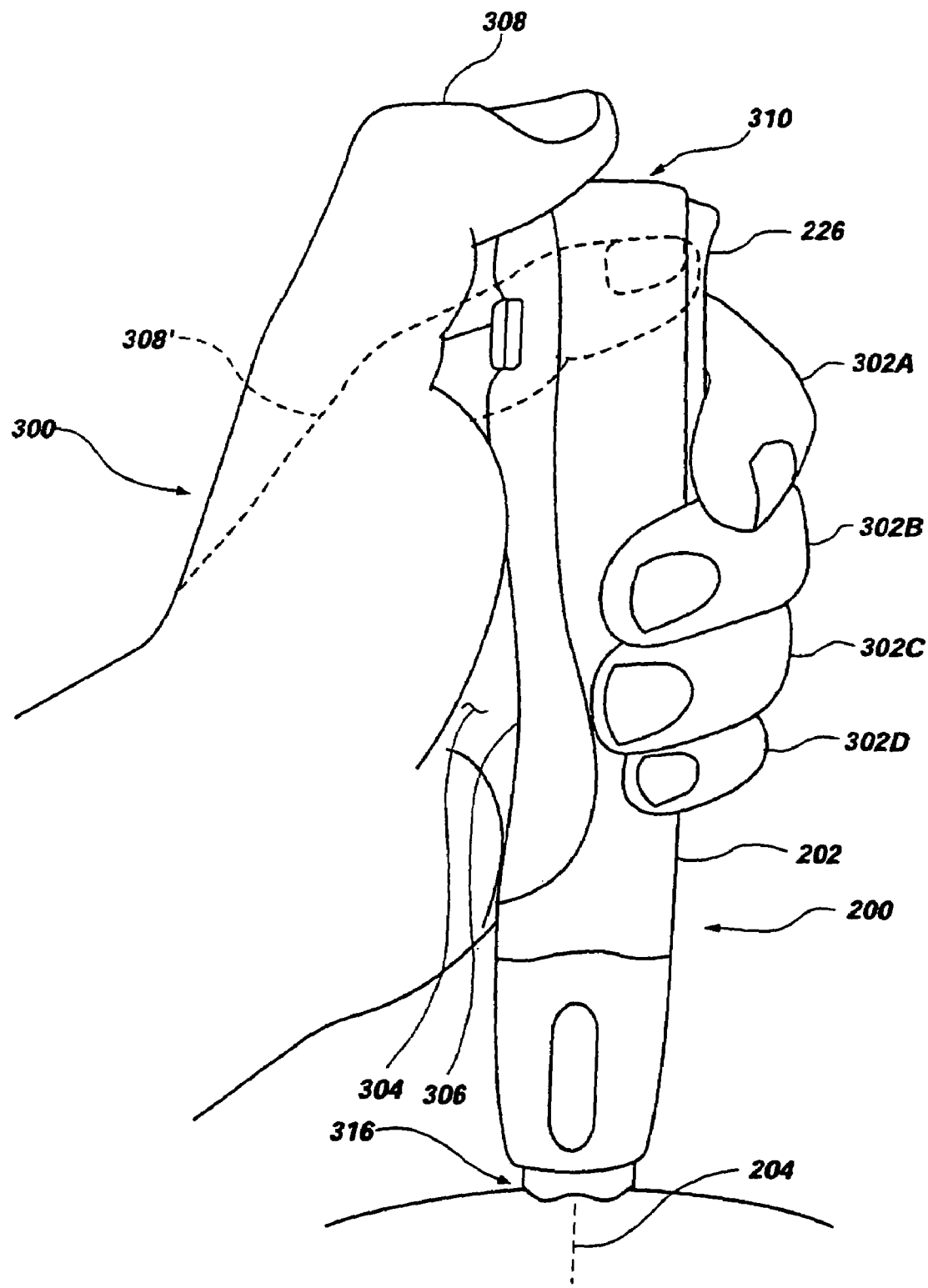

Referring now to FIGS. 10A-10C, the general use of the injection device 200 in administering an injection is shown and described in accordance with one embodiment of the present invention. Referring first to FIG. 10A, after positioning the activating member 250 to the appropriate position, a user may grasp the injection device 200 within their hand 300 so that at least one, or possibly a plurality, of the user's fingers 302A-302D, is/are wrapped about the lever 226 and such that the butt 304 of the user's hand 300 is positioned generally adjacent a surface 306 of the housing 202 which is opposite the lever 226 (referred to herein as the back-side surface 306 for purposes of convenience). It is noted that the back-side surface 306 may be ergonomically contoured to generally compliment a user's hand 300 when gripped thereby. Similarly, the lever 226 may be ergonomically contoured to generally compliment a user's hand 300 when grasped thereby.

The user's thumb 308 may be positioned at an end 310 of the injection device 200 opposite the needle end 312 of thereof. Additionally, a user may grasp the housing 202 with one or more fingers (e.g., finger 302D) at a location between lever 226 and the needle end 312 of the injection device 200. Thus, in operation, some of the user's fingers (e.g., 302A and 302B) may be positioned to actuate the lever 226, while some of the user's fingers (e.g., 302C and 302D) may be grasping the housing 202. In another embodiment, all of the user's fingers 302A-302D may be positioned on the lever 226, if so desired.

With the injection device 200 properly positioned in the user's hand 300, a user may displace the injection device 200 in the direction indicated by arrow 314. As depicted in FIG. 10B, this displacement of the injection device 200 may be accomplished by application of an appropriate force by the user's hand 300, wherein the user's thumb 308 and/or any of the user's fingers (e.g., finger 302D) are positioned about the housing 202 to provide a resistive force to the housing 202 as the injection device 200 is positioned against a user's skin at the intended site of injection 316 and the needle 204 (shown as a dashed line) is inserted therein.

Referring now to FIG. 10C, after insertion of the needle 204 into the user's skin the user may squeeze the injection device 200 within their hand 300. The squeezing action performed by the user results in the lever 226 being depressed or displaced generally toward the palm or butt 304 of a user's hand 300 by one or more fingers (e.g., fingers 302A and 302B) positioned on the lever 226. As previously described herein, such displacement of the lever 226 causes disposal of a desired amount of fluid product through the needle 204. In one particular embodiment, the user may be required to hold the lever 226 in the depressed position for a predetermined amount of time in order to ensure complete delivery of the desired volume of fluid product through the needle 204. After delivery of the fluid product through the injection needle 204, the user may withdraw the needle 204 from their skin to complete the injection process.

Still referring to FIGS. 10A-10C, an alternate hand position is also disclosed. For some individuals having impaired hand function, it may be difficult to place their thumb 308 over the end 310 of the injection device 200. Thus, as indicated by the alternate position (shown in dashed lines in FIGS. 10A-10C), it may be desirable to place the thumb 308' on a side surface of the injection device 200. The user's thumb 308' and any of the user's fingers (e.g., finger 302D) may then grip the housing 202 of the injection device to provide a resistive force to the housing 202 as the injection device 200 is positioned against a user's skin at the intended site of injection 316 and the needle 204.

Such a method of administering an injection, in conjunction with the exemplary injection device 200, enables a user thereof to grasp the injection device within their hand 300, insert the needle 204 into their skin, actuate the lever 226, and withdraw the needle 204 from their skin while maintaining substantially the same hand position relative to the injection device 200 throughout the entire process if so desired. More particularly, a user need not reposition their hand 300 relative to the device 200 between the acts of inserting the needle 204 into their skin and actuating the lever 226 (and, thus, actuating the dispensing mechanism 210—FIGS. 3 and 4). Such a feature is found to be valuable to numerous users of injection devices including, for example, those with impaired hand function.

It is additionally noted that the efficiency of the above-described injection process is enabled, in part, by the placement of the fulcrum 232 (FIGS. 3 and 4) of the lever 226 such that it is either between the intended position of the user's hand 300 and the injection needle 204, or at least between the injection needles 204 and the finger or fingers which are positioned on the lever for the actuation thereof. Such a configuration helps to prevent any inadvertent actuation of the lever 226 due to the resistive force applied by a user's hand.

Figure 11A:
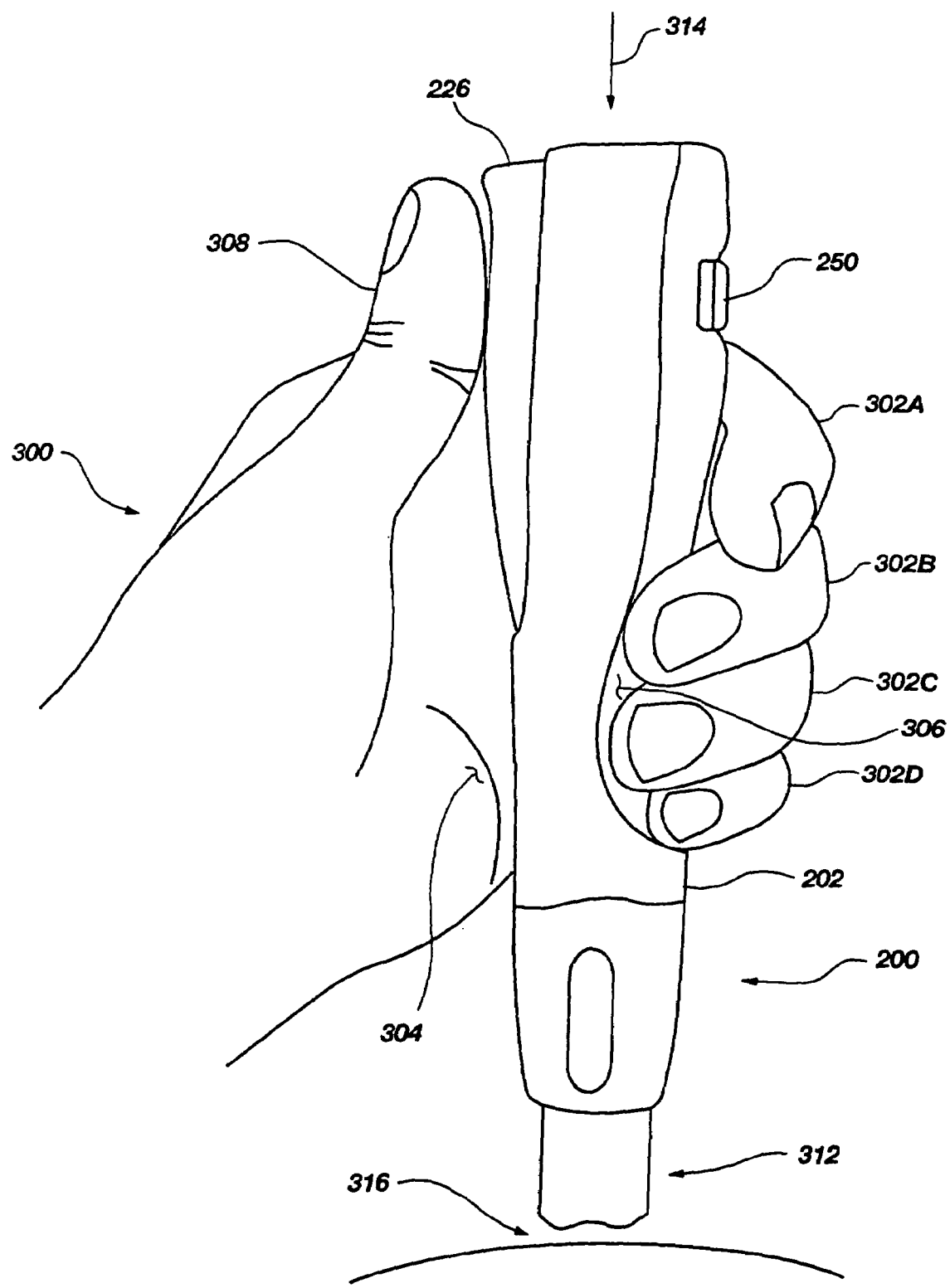
FIGS. 11A-11C depict the use of an injection device in accordance with an embodiment of the present invention.
Figure 11B:
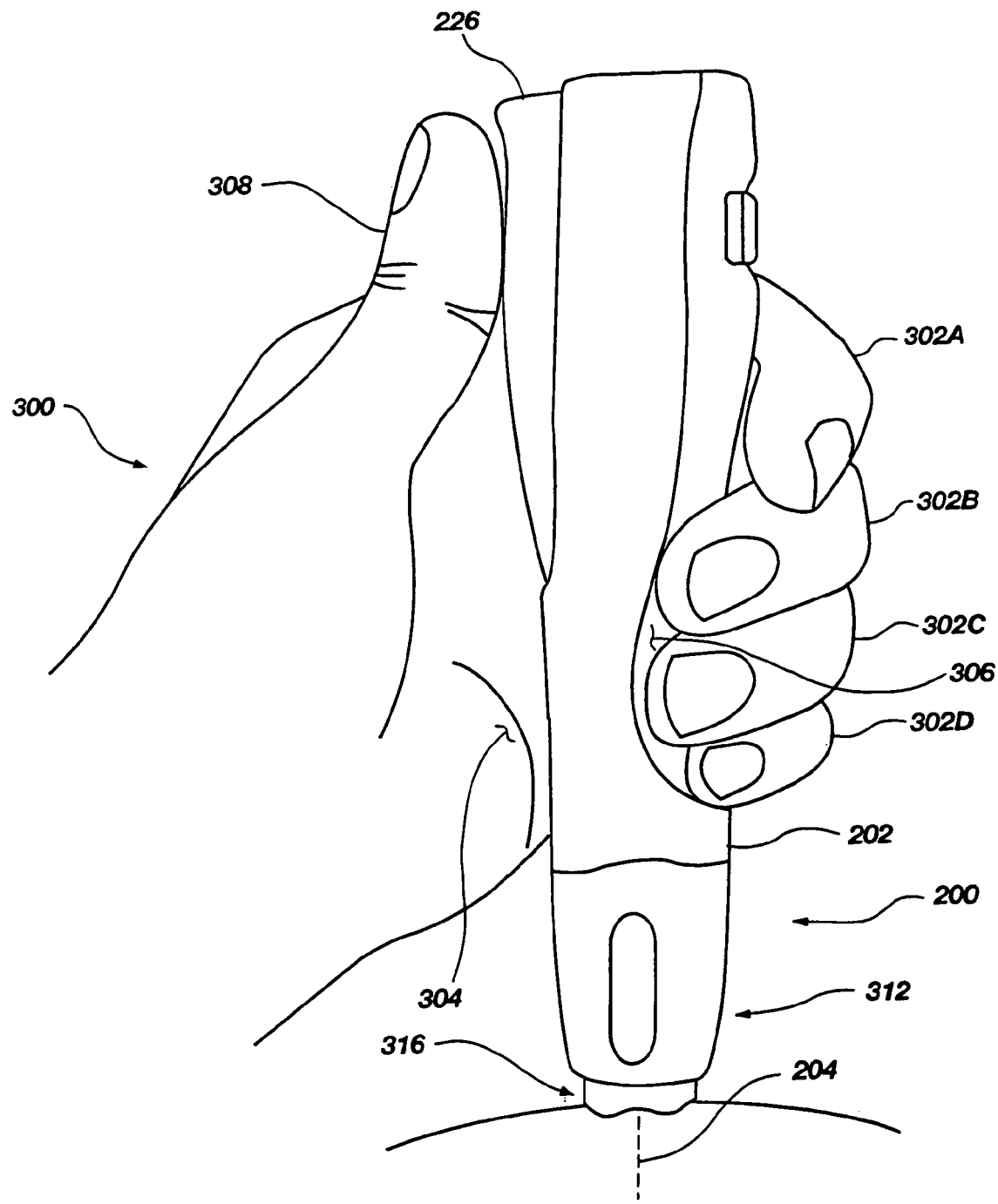
Figure 11C:
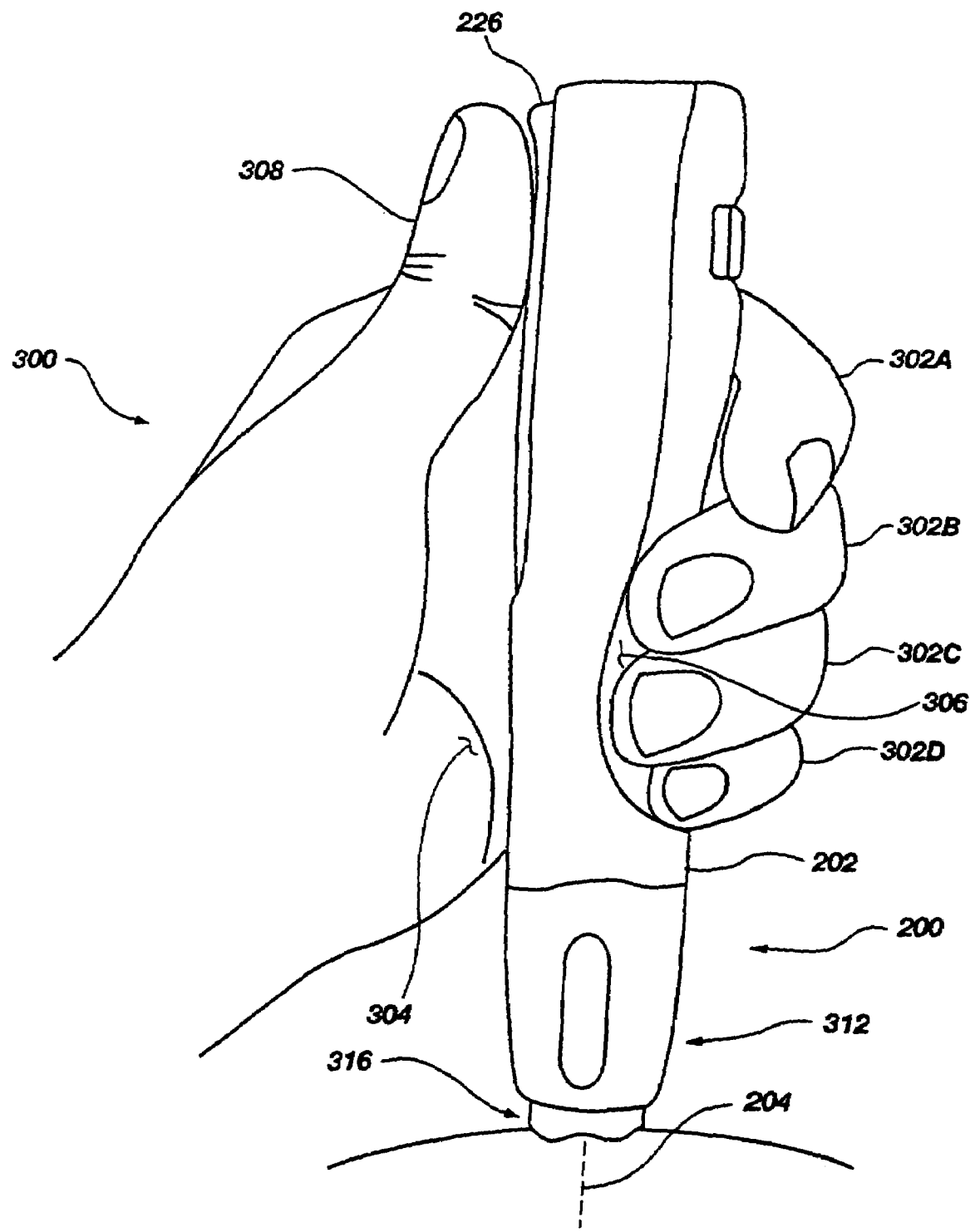

Referring now to FIGS. 11A-11C, the use of the injection device 200 in administering an injection is shown and described in accordance with another embodiment of the present invention. Referring first to FIG. 11A, after positioning the activating member 250 to the appropriate position, a user may grasp the injection device 200 within their hand 300 such that the user's fingers 302A-302D are wrapped about the back-side surface 306 and the butt 304 of the user's hand 300 is positioned generally adjacent a surface of the housing 202 between the lever 226 and the needle end 312 of the injection device 200. The user's thumb 308 may be positioned on the lever 226. In operation, the user's thumb 308 may be positioned to actuate the lever 226 while some of the user's fingers 302A-302D may grasp the housing 202.

With the injection device 200 properly positioned in the user's hand 300, a user may displace the injection device 200 in the direction indicated by arrow 314. As depicted in FIG. 11B, this displacement of the injection device 200 may be accomplished by application of an appropriate force by the user's hand 300 wherein the user's fingers 302A-302D which are positioned about the housing 202, may provide a resistive force to the housing 202 as the injection device 200 is positioned against a user's skin at the intended site of injection 316 and the needle 204 (shown as a dashed line) is inserted therein.

Referring now to FIG. 11C, after insertion of the needle 204 into the user's skin, the user may squeeze the injection device 200 within their hand 300 and depress the lever 226 with their thumb 308. As previously described herein, such displacement of the lever 226 causes disposal of a desired amount of fluid product through the needle 204. In a particular embodiment, the user may be required to hold the lever 226 in the depressed position for a predetermined amount of time in order to ensure complete delivery of the desired volume of fluid product through the needle 204. After delivery of the fluid product through the injection needle 204, the user may withdraw the needle 204 from their skin to complete the injection process.

Again, such a method of administering an injection, in conjunction with the exemplary injection device 200, enables a user thereof to grasp the injection device within their hand 300, insert the needle 204 into their skin, actuate the lever 226, and withdraw the needle 204 from their skin while maintaining substantially the same hand position relative to the injection device 200 throughout the entire process. More particularly, a user need not reposition their hand 300 relative to the device 200 between the acts of inserting the needle 204 into their skin and actuating the lever 226 (and, thus, actuating the dispensing mechanism 210—FIGS. 3 and 4).

More generally, the use of the injection device 200 in accordance with the above-described methods may be characterized as grasping the housing 202 of the injection device 200 with at least one digit of a user's hand 300 (i.e., at least one of the thumb 308 and fingers 302A-302D) and positioning at least one other digit of the user's hand on the lever 226. The at least one digit which grasps the housing 202 may provide a resistive force when inserting the needle 204 into the user's skin and the at least one other digit may be used to actuate the lever 226 subsequent such insertion without the need to reposition the user's hand relative to the injection device 200.

Additional features of the exemplary injection device 200 may also enhance the usability of the same for individuals with poor motor skills or impaired hand function. For example, the injection device 200 may be configured to fit comfortably within a users hand both in terms of its circumferential dimensions as well as the length of the housing 202 and the length of the lever 226. In one exemplary embodiment, referring to FIG. 3, the maximum depth X from the face of the lever 226 to the opposing surface may be approximately 40 mm (approximately 1.57 inches) when the lever 226 is in the first position (FIG. 5A). Referring to FIG. 6, in one embodiment, the length Y of the exemplary injection device 200 may be approximately 155 mm (approximately 6.10 inches) and the width Z may be approximately 27 mm (approximately 1.06 inches).

Referring back to FIG. 3, in one embodiment, the engageable length $L_1$ of the lever 226 or the length of the portion of the lever which is exposed for engagement by a user's hand may be approximately 63 mm (approximately 2.48 inches). The overall length $L_2$ of the lever 226, or the length of the lever 226 extending from the fulcrum 232, may be approximately 85 mm (approximately 3.35 inches).

Additionally, referring to FIG. 5B, the stroke S, or the distance through which the lever 226 travels to effect the desired dispensing of fluid product through the injection needle 204, may be approximately 6 mm (approximately 0.25 inches). Stated another way, the lever 226 may be configured to rotate through an angle of approximately 4° about its fulcrum 232. Furthermore, the lever 226 may be configured to require a specified magnitude of force for the displacement and actuation thereof. In one example, a required force of approximately 15 N to 20 N, as applied to the lever at a location adjacent the distal end with respect to the fulcrum 232 may be required for proper actuation of thereof.

More specifically, the application of a specified moment to the lever may optionally be required for actuation thereof. For example, in one embodiment, a moment of approximately 1.275 Nm to 1.70 Nm may be required to displace the lever 226 the desired stroke distance S.

Generally, with regards to providing an injection device and method of injection for individuals with impaired hand function or deteriorated motor skills, it is desirable to minimize the magnitude of force which is required for displacement of the lever 226. Such may be accomplished, for example, by providing a lever 226 with a longer overall length $L_2$ and, therefore, a larger stroke distance S. However, because some individuals have difficulty opening their hands to a substantial extent, it may also be desirable to limit the stroke distance S and maximum depth X so as to enable patients with limited hand mobility to use such an injection device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method of administering an injection, the method comprising:
   providing an injection device having a housing comprising a first end and a second end, the injection device further including a needle disposed proximate the second end, a dispensing mechanism having a cap that drives the dispensing mechanism when displaced from a first position to a second position along a longitudinal axis defined between the first end of the housing and the second end of the housing, the cap circumferentially positioned around the longitudinal axis and an actuator disposed between the first and second end, wherein the actuator comprises a first end rotatably coupled to the housing at a pivot and a second end disposed in closer proximity to the first end of the housing than the first end of the actuator, the second end of the actuator having a protrusion extending into the housing at the first end of the injection device, the protrusion having an interfacing surface at an oblique angle relative to the longitudinal axis, the interfacing surface configured to interact with the cap to cause the displacement thereof from the first position to the second position along the longitudinal axis upon rotation of the actuator about the pivot, wherein the dispensing mechanism further has a biasing member configured to displace the cap back along the longitudinal axis from the second position to the first position preparatory to a subsequent displacement from the first position to the second position by the interfacing surface of the actuator;
   grasping the injection device and establishing a hand position, wherein establishing a hand position includes placing a thumb at the first end of the housing substantially in opposition of the second end of the housing and placing at least one finger on the actuator;
   applying a force to the injection device with at least the thumb while inserting the needle into a portion of skin; and
   substantially maintaining the established hand position while displacing the actuator with the at least one finger in a direction substantially transverse to the longitudinal axis, wherein displacing the actuator changes a contact point of the cap along the interfacing surface of the protrusion of the actuator and thereby converts transverse displacement of the actuator into longitudinal displacement of the cap of the dispensing mechanism to effect delivery of a fluid product through the needle, wherein the pivot about which the actuator rotates is located between the second end of the housing and the at least one finger.

2. The method according to claim 1, wherein placing at least one finger on the actuator includes placing a plurality of fingers on the actuator.

3. The method according to claim 1, wherein placing at least one finger on the actuator includes placing four fingers on the actuator.

4. The method according to claim 1, wherein establishing a hand position further includes grasping the housing about a surface thereof with at least one other finger.

5. The method according to claim 4, wherein applying a force to the injection device at least through the thumb includes applying a force in a direction of the second end through the thumb and through the at least one other finger.

6. The method according to claim 1, wherein displacing the actuator includes rotating the actuator through an angle of approximately 4 degrees.

7. The method according to claim 1, wherein displacing the actuator includes displacing the second end of the actuator a distance of approximately 6 millimeters.

8. The method according to claim 1, wherein displacing the actuator further includes applying a force of approximately 15 to 20 Newtons to the actuator proximate the second end thereof.

9. The method according to claim 1, wherein displacing the actuator further includes applying a moment of approximately 1.275 to 1.70 Newton-meters to the actuator.

10. The method according to claim 1, wherein providing an injection device includes providing an injection device with an activating member configured to activate the actuator, and wherein the method includes displacing the activating member prior to establishing the hand position.

11. The method according to claim 1, further comprising removing the needle from the portion of skin.

12. A method of administering an injection, the method comprising:
providing an injection device having a housing comprising a first end and a second end, the injection device further including a needle disposed proximate the second end, a dispensing mechanism having a cap that drives the dispensing mechanism when displaced from a first position to a second position along a longitudinal axis defined between the first end of the housing and the second end of the housing, the cap circumferentially positioned around the longitudinal axis and an actuator disposed between the first and second end, wherein the actuator comprises a first end rotatably coupled to the housing at a fulcrum and a second end disposed in closer proximity to the first end of the housing than the first end of the actuator, the second end of the actuator having a protrusion extending into the housing at the first end of the injection device, the protrusion having an interfacing surface at an oblique angle relative to the longitudinal axis, the interfacing surface configured to interact with the cap to cause the displacement thereof from the first position to the second position along the longitudinal axis upon pivoting of the actuator about the fulcrum, wherein the dispensing mechanism further has a biasing member configured to displace the cap back along the longitudinal axis from the second position to the first position preparatory to a subsequent displacement from the first position to the second position by the interfacing surface of the actuator;
grasping the injection device and establishing a hand position, wherein establishing a hand position includes placing at least one digit around a portion of the housing at a location between the first end of the housing and the second end of the housing and placing at least one other digit on the actuator;
applying a force to the injection device in the direction of the needle through the at least one digit while inserting the needle into a portion of skin; and
substantially maintaining the established hand position while displacing the actuator with the at least one other digit in a direction substantially transverse to the longitudinal axis, wherein displacing the actuator changes a contact point of the cap along the interfacing surface of the protrusion of the actuator and thereby converts transverse displacement of the actuator into longitudinal displacement of the cap of the dispensing mechanism to effect delivery of a fluid product through the needle, wherein the fulcrum about which the actuator pivots is located between the second end of the housing and the at least one digit.

13. The method according to claim 12, wherein applying a force to the injection device includes applying a frictional force to the surface of the injection device through the at least one digit.

14. The method according to claim 12, wherein placing at least one digit around a portion of the housing includes placing a plurality of fingers around a portion of the housing.

15. The method according to claim 12, wherein placing at least one other digit on the actuator includes placing a plurality of fingers on the actuator.

16. The method according to claim 12, wherein placing at least one other digit on the actuator includes placing a thumb on the actuator.

17. The method according to claim 12, wherein establishing a hand position further includes positioning a thumb on a surface of the housing.

18. The method according to claim 17, wherein applying a force to the injection device includes applying a force through the thumb.

19. The method according to claim 12, wherein displacing the actuator includes rotating the actuator through an angle of approximately 4 degrees.

20. The method according to claim 12, wherein displacing the actuator includes displacing the second end of the actuator a distance of approximately 6 millimeters.

21. The method according to claim 12, wherein displacing the actuator further includes applying a force of approximately 15 to 20 Newtons to the actuator proximate the second end thereof.

22. The method according to claim 12, wherein displacing the actuator further includes applying a moment of approximately 1.275 to 1.70 Newton-meters to the actuator.

23. The method according to claim 14, wherein providing an injection device includes providing an injection device with an activating member configured to activate the actuator, and wherein the method includes displacing the activating member prior to establishing the hand position.

24. The method according to claim 14, further comprising removing the needle from the portion of skin.

25. A method of administering an injection, the method comprising:
providing an injection device having a housing, the housing having a first end and a second end, the injection device further including a needle disposed proximate the second end, a dispensing mechanism having a cap that drives the dispensing mechanism when displaced from a first position to a second position along a longitudinal axis defined between the first end of the housing and the second end of the housing, the cap circumferentially positioned around the longitudinal axis and an actuator disposed between the first and second end, wherein the actuator comprises a first end rotatably coupled to the housing at a pivot and a second end disposed in closer proximity to the first end of the housing than the first end of the actuator, the second end of the actuator having a protrusion extending into the housing at the first end of the injection device, the protrusion having an interfacing surface at an oblique angle relative to the longitudinal axis, the interfacing surface configured to interact with the cap to cause the displacement thereof from the first position to the second position along the longitudinal axis upon rotation of the actuator about the pivot, wherein the dispensing mechanism further has a biasing member configured to displace the cap back along the longitudinal axis from the second position to the first position preparatory to a subsequent displacement from the first position to the second position by the interfacing surface of the actuator;

grasping the injection device and establishing a hand position, wherein establishing a hand position includes placing at least one digit around a portion of the housing at a location between the first end of the housing and the second end of the housing and placing at least one other digit on the actuator;

applying a force to the injection device in the direction of the needle through the at least one digit while inserting the needle into a portion of skin; and displacing the actuator with the at least one other digit in a direction substantially transverse to the longitudinal axis to effect delivery of a fluid product through the needle including rotating the actuator about the pivot, wherein the pivot is located between the second end of the housing and the at least one digit, wherein rotating the actuator changes a contact point of the cap along the interfacing surface of the protrusion of the actuator and thereby converts transverse displacement of the actuator into longitudinal displacement of the cap of the dispensing mechanism to drive the dispensing mechanism.

26. The method according to claim 25, further comprising substantially maintaining the established hand position while inserting the needle and displacing the actuator.

27. The method according to claim 25, further comprising removing the needle from the portion of skin.

* * * * *